US009289308B2

(12) United States Patent
Marino et al.

(10) Patent No.: US 9,289,308 B2
(45) Date of Patent: Mar. 22, 2016

(54) ARTICULATING INTERBODY CAGE AND METHODS THEREOF

(75) Inventors: James F. Marino, San Diego, CA (US); Jamil Elbanna, San Diego, CA (US)

(73) Assignee: Trinity Orthopedics, LLC, San Diego, CA (US)

(*) Notice: Subject to any disclaimer, the term of this patent is extended or adjusted under 35 U.S.C. 154(b) by 204 days.

(21) Appl. No.: 14/007,954

(22) PCT Filed: Mar. 30, 2012

(86) PCT No.: PCT/US2012/031693
§ 371 (c)(1),
(2), (4) Date: Sep. 26, 2013

(87) PCT Pub. No.: WO2012/135764
PCT Pub. Date: Oct. 4, 2012

(65) Prior Publication Data
US 2014/0018922 A1    Jan. 16, 2014

Related U.S. Application Data

(60) Provisional application No. 61/469,778, filed on Mar. 30, 2011.

(51) Int. Cl.
*A61F 2/44*    (2006.01)
*A61F 2/46*    (2006.01)
(Continued)

(52) U.S. Cl.
CPC . *A61F 2/44* (2013.01); *A61F 2/447* (2013.01); *A61F 2/4611* (2013.01);
(Continued)

(58) Field of Classification Search
CPC .................................. A61F 2/44; A61F 2/447
USPC ............................................. 623/17.11–17.16
See application file for complete search history.

(56) References Cited

U.S. PATENT DOCUMENTS 6,126,689 A * 10/2000 Brett ..................... A61F 2/4455
                                                        623/17.15
8,147,499 B2 * 4/2012 Zubok .................. A61B 17/025
                                                        606/57

(Continued)

FOREIGN PATENT DOCUMENTS

WO    WO-2005/120400 A2    12/2005
WO    WO-2009/114523 A1    9/2009
(Continued)

OTHER PUBLICATIONS

International Search Report and Written Opinion for PCT/US2012/031693 dated Jun. 26, 2012.

*Primary Examiner* — Christopher Beccia
(74) *Attorney, Agent, or Firm* — Fred C. Hernandez; Mintz Levin Cohn Ferris Glovsky and Popeo, P.C.

(57) ABSTRACT

Disclosed herein are devices (100), systems and methods of use relating to articulating interbody cages. In one aspect, disclosed is an intervertebral device (100) for use in a human spine including an anterior end (104); a posterior end (102); and at least four peripheral walls (22,24,26). The peripheral walls (26) define an interior volume surrounding a midline of the device and include a superior wall (22), an inferior wall (24) and a pair of opposing, generally trapezoidal-shaped sidewalls. Each of the trapezoidal-shaped sidewalls (26) includes an internal hinge element (60) that is rotatable from a first configuration to at least a second configuration such that the device is expandable in first dimension. Each of the internal hinge elements includes an axis that is coplanar with the midline of the device.

19 Claims, 40 Drawing Sheets

(51) Int. Cl.
*A61F 2/28* (2006.01)
*A61F 2/30* (2006.01)

(52) U.S. Cl.
CPC *A61F 2002/2817* (2013.01); *A61F 2002/2835* (2013.01); *A61F 2002/30019* (2013.01); *A61F 2002/30179* (2013.01); *A61F 2002/30205* (2013.01); *A61F 2002/30265* (2013.01); *A61F 2002/30266* (2013.01); *A61F 2002/30464* (2013.01); *A61F 2002/30466* (2013.01); *A61F 2002/30471* (2013.01); *A61F 2002/30477* (2013.01); *A61F 2002/30492* (2013.01); *A61F 2002/30528* (2013.01); *A61F 2002/30579* (2013.01); *A61F 2002/30616* (2013.01); *A61F 2002/30632* (2013.01); *A61F 2002/30637* (2013.01); *A61F 2002/30785* (2013.01); *A61F 2002/30789* (2013.01); *A61F 2002/4475* (2013.01); *A61F 2002/4627* (2013.01); *A61F 2002/4693* (2013.01); *A61F 2310/00023* (2013.01); *A61F 2310/00047* (2013.01); *A61F 2310/00053* (2013.01); *A61F 2310/00161* (2013.01); *A61F 2310/00179* (2013.01)

(56) References Cited

U.S. PATENT DOCUMENTS

| | | |
|---|---|---|
| 2003/0171813 A1 | 9/2003 | Kiester |
| 2005/0131536 A1 | 6/2005 | Eisermann et al. |
| 2008/0021559 A1 | 1/2008 | Thramann |
| 2008/0077242 A1* | 3/2008 | Reo ............ A61F 2/441 623/17.15 |
| 2008/0243255 A1 | 10/2008 | Butler et al. |
| 2009/0157187 A1* | 6/2009 | Richelsoph ........ A61F 2/4455 623/17.16 |
| 2009/0222100 A1 | 9/2009 | Cipoletti et al. |
| 2010/0185291 A1 | 7/2010 | Jimenez et al. |
| 2011/0035011 A1 | 2/2011 | Cain |

FOREIGN PATENT DOCUMENTS

| | | |
|---|---|---|
| WO | WO-2009/125242 A1 | 10/2009 |
| WO | WO-2010/078468 A2 | 7/2010 |

* cited by examiner

ARTICULATING INTERBODY CAGE AND METHODS THEREOF

REFERENCE TO PRIORITY DOCUMENT

This application claims the benefit of priority under 35 U.S.C. 119(e) of U.S. Provisional Patent Application Ser. No. 61/469,778, filed Mar. 30, 2011. Priority of the aforementioned filing date is hereby claimed and the disclosure of the provisional patent application is hereby incorporated by reference in its entirety.

BACKGROUND

A significant number of adults have had an episode of back pain or suffer chronic back pain emanating from a region of the spinal column. A number of spinal disorders are caused by traumatic spinal injuries, disease processes, aging processes, and congenital abnormalities that cause pain, reduce the flexibility of the spine, decrease the load bearing capability of the spine, shorten the length of the spine, and/or distort the normal curvature of the spine. Many people suffering from back pain resort to surgical intervention to alleviate their pain.

Disc degeneration can contribute to back pain. With age, the nucleus pulposus of the intervertebral discs tends to become less fluid and more viscous. Dehydration of the intervertebral disc and other degenerative effects can cause severe pain. Annular fissures also may be associated with a herniation or rupture of the annulus causing the nucleus to bulge outward or extrude out through the fissure and impinge upon the spinal column or nerves (i.e. a "ruptured" or "slipped" disc).

In addition to spinal deformities that can occur over several motion segments, spondylolisthesis (i.e. forward displacement of one vertebra over another, usually in the lumbar or cervical spine) is associated with significant axial and/or radicular pain. Patients who suffer from such conditions can experience diminished ability to bear loads, loss of mobility, extreme and debilitating pain, and oftentimes suffer neurological deficit in nerve function.

Failure of conservative therapies to treat spinal pain such as for example bed rest, pain and muscle relaxant medication, physical therapy or steroid injection often urges patients to seek spinal surgical intervention. Many surgical techniques, instruments and spinal disc implants have been described that are intended to provide less invasive, percutaneous, or minimally-invasive access to a degenerated intervertebral spinal disc. Instruments are introduced through the annulus for performing a discectomy and implanting bone growth materials or biomaterials or spinal disc implants within the annulus. One or more annular incisions are made into the disc to receive spinal disc implants or bone growth material to promote fusion, or to receive a pre-formed, artificial, functional disc replacement implant.

Extensive perineural dissection and bone preparation can be necessary for some of these techniques. In addition, the disruption of annular or periannular structures can result in loss of stability or nerve injury. As a result, the spinal column can be further weakened and/or result in surgery-induced pain syndromes.

Various posterior interbody approaches such as posterior lumbar interbody fusion (PLIF) and transforaminal lumbar interbody fusion (TLIF) necessitate placing an interbody device through a relatively small annular aperture from a posterior access dissection path. The desire to restore disc space height and create lordosis through anterior distraction is in conflict with the application of a fixed height interbody spacer through a limited posterior approach. In addition, the larger the "foot-print" of the interbody spacer, the less likely it will subside. This is not only due to reduced endplate pressure but also better load bearing bone near the perimeter of the endplate (versus the central region).

SUMMARY

In one aspect, disclosed is an intervertebral device for use in a human spine. The device includes an anterior end; a posterior end; and at least four peripheral walls defining an interior volume surrounding a midline of the device. The peripheral walls include a superior wall, an inferior wall and a pair of opposing, generally trapezoidal-shaped sidewalls. Each of the trapezoidal-shaped sidewalls includes an internal hinge element that is rotatable from a first configuration to at least a second configuration such that the device is expandable in first dimension. Each of the internal hinge elements includes an axis that is coplanar with the midline of the device.

The device can be additionally expandable in a second dimension. The first dimension can include a caudal-cephalad dimension and the second dimension can include a medial-lateral dimension. Each of the internal hinge elements can be positioned along the midline of its respective sidewall. The superior wall and the inferior wall each can mate with the pair of opposing sidewalls at a rotatable joint. The internal hinge element can couple a superior plate element to an inferior plate element. Each of the internal hinge elements further can include a plurality of overhangs configured to restrict articulation from the first configuration to the second configuration. The cephalad surface of the superior wall can be configured to engage a first vertebra of the human spine. At least a portion of the caudal surface of the inferior wall can be configured to engage a second vertebra of the human spine. The cephalad surface of the superior wall and the caudal surface of the inferior wall can be configured to penetrate the respective superior and inferior endplates.

The cephalad surface of the superior wall and the caudal surface of the inferior wall can include projection elements that engage the respective superior and inferior vertebral endplates. The projection elements can include a wedge shape and provide additional separation between the superior and inferior vertebral endplates. The projection elements can include a tapered distal tip. The outer surfaces of the pair of opposing sidewalls can include projection elements. The projection elements can impart further stiffness to the opposing sidewalls. The generally trapezoidal-shaped sidewalls can be oriented relative to the spine such that the longer segment is anterior and the shorter segment is posterior. The device can create a desired lordosis in the spine. Each of the at least four peripheral walls can be generally trapezoidal-shaped. The internal hinge element can include a plurality of ridge elements that form a linear track upon expansion of the intervertebral device to the second configuration. The internal hinge element can further include a plurality of overhangs configured to restrict articulation from the first configuration to the second configuration.

The device can further include a brace configured to be positioned within the interior volume of the intervertebral device to support the intervertebral device under load. The brace can include a cylindrical element having a tapered outer diameter such that when positioned in the interior volume the brace is larger near the anterior region than the posterior region. The brace element can have a fixed dimension. The brace element can prevent one or more of the peripheral walls from articulating from the second configuration towards the first configuration. The brace element can be configured to be translated from an initial introductory orientation to a final stabilization orientation. The brace element can include fenestrations configured to permit growth of tissue from one vertebral endplate to a second vertebral endplate.

In an interrelated aspect, disclosed is a method of treating a spine. The method includes positioning an intervertebral device in a first configuration into a space between adjacent vertebrae. The intervertebral device includes an anterior end, a posterior end, and at least four peripheral walls defining an interior volume. The peripheral walls include a superior wall, an inferior wall and a pair of opposing sidewalls. At least two of the peripheral walls are generally trapezoidal. The opposing sidewalls include an articulation mechanism having a plurality of hinges. The first configuration includes the plurality of hinges articulated to minimize the interior volume of the intervertebral device. The method also includes inserting a brace through the interior volume of the intervertebral device in a posterior to anterior direction to deploy the intervertebral device into a second configuration to separate the adjacent vertebrae and create a desired lordosis in the spine. The second configuration includes an interior volume that is larger than when the device is in the first configuration. The method includes locking the brace such that the plurality of hinges is prevented by the brace from articulating into the first configuration.

The method can further include inserting an elongate tool into the interior volume to expand the device towards the second configuration prior to inserting the brace. Inserting the elongate tool can include using a tapered projecting tip on the elongate tool to pry open and at least partially articulate the plurality of hinges. The method can further include expanding an elastomeric element on the elongate tool using hydraulic pressure. The method can further include collapsing the elastomeric element on the elongate tool and withdrawing the tool through a central bore extending through a longitudinal axis of the brace.

In an interrelated aspect, disclosed is a device including caudal and cephalad plates that are positioned adjacent to vertebral endplates within an intervertebral disc space. The device includes lateral walls attached to the caudal and cephalad plates via an articulating mechanism. At least one of the lateral walls includes a hinge element restricted from achieving an on-center or over-center articulation position. The device is configured to be inserted into an intervertebral disc space in a reduced dimension configuration and subsequently expanded to an enlarged dimension configuration.

One or more of the caudal plate, cephalad plate, and lateral walls can be relatively radiolucent. The device can further include one or more osteoinductive, osteoproliferative, osteoconductive materials positioned internal to the device and extending from a caudal vertebral endplate to a cephalad vertebral endplate. One or both of the caudal and cephalad plates can include an external textured surface. The enlarged dimension configuration can be dimensionally expanded along an axis or arc other than that associated with caudal-cephalad expansion.

In an interrelated aspect, disclosed is a device including caudal and cephalad plates that are positioned adjacent to vertebral endplates within an intervertebral disc space, and at least two lateral walls attached to the caudal and cephalad plates via an articulating mechanism. The device includes an internal brace positioned between the plates and the at least two lateral walls. Caudal-cephalad compressive loading of the device results in compression of the internal brace along axes extending between the caudal and cephalad plates as well as between at least two lateral walls. The device is configured to be inserted into an intervertebral disc space in a reduced dimension configuration and subsequently expanded to an enlarged dimension configuration.

One or more of the caudal plate, cephalad plate, and lateral walls can be relatively radiolucent. The device can further include one or more osteoinductive, osteoproliferative, osteoconductive materials positioned internal to the device and extending from a caudal vertebral endplate to a cephalad vertebral endplate. One or both of the caudal and cephalad plates can include an external textured surface. The enlarged dimension configuration can be dimensionally expanded along an axis or arc other than that associated with caudal-cephalad expansion.

BRIEF DESCRIPTION OF THE DRAWINGS

Reference is made to the following description, taken in conjunction with the accompanying drawings, in which like reference characters refer to like parts throughout.

Figure 1A:
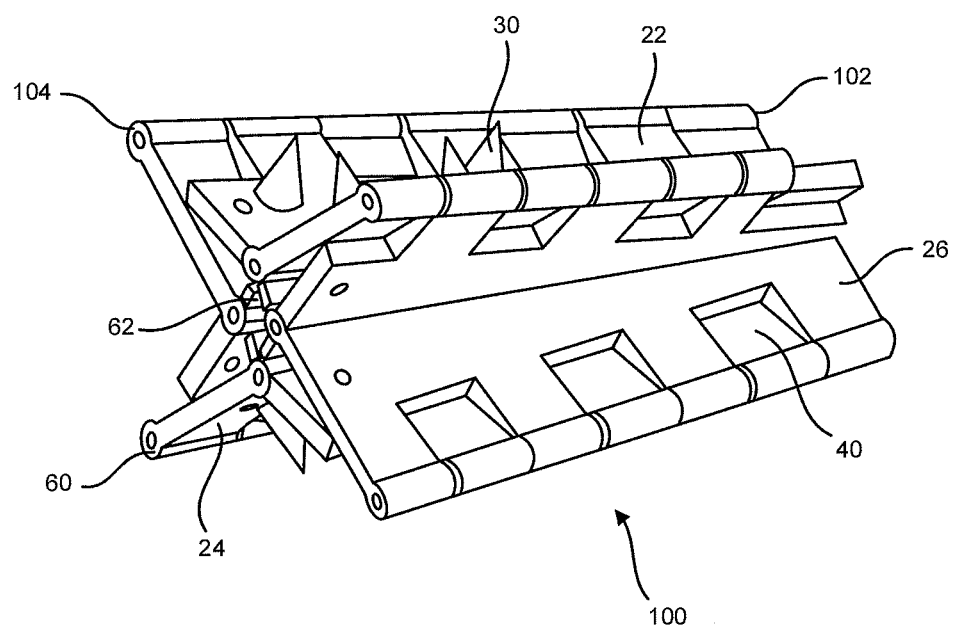
FIGS. 1A to 1D provide a side perspective view of an intervertebral device from a fully collapsed configuration (FIG. 1A) to a fully expanded configuration (FIG. 1D).
Figure 1B:
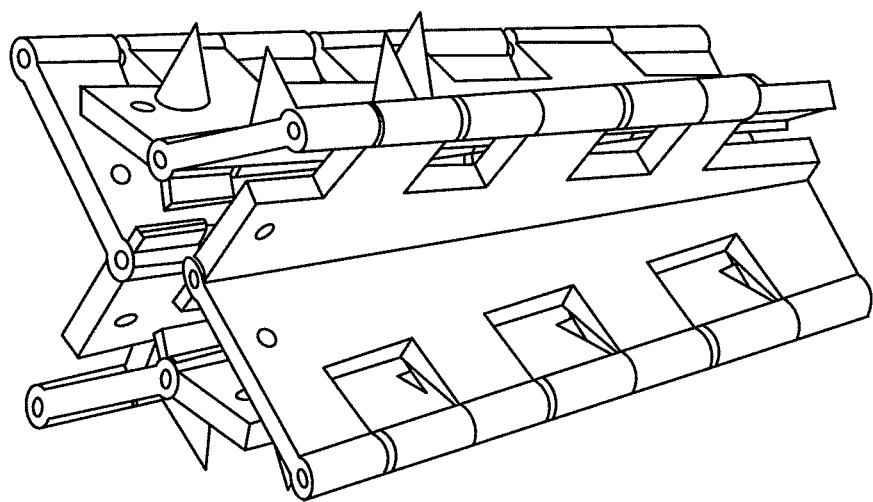

It is to be understood that implants described herein may include features not necessarily depicted in each figure. In some embodiments, an endplate engaging surface of any implant may have regularly or irregularly spaced protrusions of uniform or various shapes and sizes to facilitate retention of the implant in a desired position between vertebrae.

DETAILED DESCRIPTION

The devices and methods described herein can address the surgical desire to implant an interbody cage through a relatively small posterior access annulotomy, while providing for lordotic inducing disc space distraction and an expanded "foot-print" for endplate support. The devices described herein can be initially delivered into the disc space, in a collapsed or folded form and then expanded in situ.

The shape and/or size of an implant or other device disclosed herein may be chosen according to factors including, but not limited to, the surgical approach employed for insertion, the intended position in the spine, and a size of the patient. For example, intervertebral devices may range from about 6 mm to about 18 mm in height (e.g., 7 mm, 8 mm, 9 mm, 10 mm, 10.5 mm, 11 mm, 12 mm, 13 mm, 14 mm, 15 mm, 16 mm, 17 mm). Heights outside these ranges may be used as required by a patient's anatomy. The width may range from about 8 mm to about 16 mm. Implants that are substantially rectangular or trapezoidal may range from about 9 mm to about 14 mm medial-lateral with PLIF and TLIF approaches. The height (or caudal-cephalad) dimension can be between about 9 mm to about 14 mm. It should be appreciated that the dimensions can be slightly less or slightly greater than these dimensions.

The devices described herein can be used in the vertebral column in one or more spinal motion segments, including cervical, thoracic, lumbar, and sacral regions of the spine. It should also be understood that more than one device can be implanted, for example at the same spinal motion segment or in different spinal motion segments. It should also be understood that a variety of approaches can be used to implant the devices described herein, for example anterior approach, posterior, transforaminal approaches and other approaches known in the art.

The devices described herein can be expanded such that a height of the device and/or a separation distance between two parts of the device is increased. In some embodiments, an implant may be expanded after insertion of the implant in a human spine.

The devices described herein can also articulate such that at least two members of the implant are capable of undergoing rotational motion with respect to each other in at least one direction after insertion in a human spine (e.g., a hinge design). For example, an articulating intervertebral device or cage can include segments united by joints or hinges. The devices described herein can increase in dimension both medial-lateral as well as cephalad-caudal generally along its entire anterior-posterior length by virtue of the joints or hinges associated with the four peripheral walls (medial, lateral, cephalad, and caudal).

In certain embodiments, expansion of an implant after insertion in a human spine may allow articulation of the device. That is, the intervertebral device may not display articulating motion before expansion of the implant in a human spine. In other embodiments, expansion of an implant after insertion in a human spine may allow an increased range of motion (increased articulation) between at least two members of the implant.

An implant may be constructed of one or more biocompatible metals having a non-porous quality and a smooth finish. In some embodiments, an implant may be constructed of ceramic and/or one or more other suitable biocompatible materials, such as biocompatible polymers. In certain embodiments, an implant may be constructed of a combination of one or more biocompatible metals and one or more ceramic and/or polymeric materials. In some embodiments, the device is made of implantable metal alloy materials including, but not limited to, titanium, vanadium, aluminum alloy, or titanium alloy or from implant grade biocompatible polymers including, but not limited to polyether ether ketone (PEEK). The devices described herein can be made of carbon fiber composites and polycarbonate materials.

According to some embodiments, the intervertebral device can include at least four walls, which may be described as a superior wall, an inferior wall, and two lateral or side walls. In some embodiments, the intervertebral device can include at least four walls, wherein at least two walls are hinged walls. In some embodiments, the hinged walls are opposing walls (i.e., opposing lateral or side walls; opposing superior and inferior walls; or opposing cephalic and caudal surfaces). The walls may be hinged along their respective midlines. The walls may also be hinged where they couple to one another such that a hinge is formed at each corner of the intervertebral device. In some embodiments, the intervertebral device has hinge elements at each corner where the peripheral walls meet and hinge elements along the midline of each peripheral wall.

In some embodiments, the intervertebral device can include at least four walls, wherein at least four walls are hinged walls. The walls may be hinged along their respective midlines. For example, the superior (i.e. cephalad), inferior (i.e. caudal) and lateral walls may be hinged along their respective midlines.

The intervertebral device may be symmetrical along a longitudinal axis such that the opposing walls are identical or mirror images of each other. In some embodiments, the superior (i.e. cephalad) and inferior (i.e. caudal) walls are narrower posterior than anterior. In some embodiments, each wall is narrower posterior than anterior. According to some embodiments, the anterior portion of the intervertebral device may be tapered in the saggital and transverse planes.

In some embodiments, at least two of the walls of the intervertebral device are generally trapezoidal. The parallel segments of the trapezoidal walls may be oriented such that the longer segment is anterior and the shorter segment is posterior, for example, to form a lordotic taper. In some embodiments, the trapezoidal walls are hinged, for example, along their respective midlines. In other embodiment, all peripheral walls are trapezoidal shaped and narrower at a posterior end compared to an anterior end when positioned within the spine.

In some embodiments, the intervertebral device can include a plurality of block elements that are integrated/interconnected in the hinge design. As the intervertebral device is moved from the collapsed to the expanded configuration, the block elements of the intervertebral device can give way to open areas or apertures. Further, the interior volume of the intervertebral device can be filled with materials such as bone cement, bone graft and other materials including diffusible, migratory, and osteoconductive materials. The open areas can allow egress of the material filling the interior volume. It should be appreciated, however, that the devices described herein can be used without filling of the internal volume with material.

In some embodiments, an endplate engaging surface of an implant may include teeth, spikes, ridges or other projections that can penetrate or grip the endplate. In some embodiments, members of an implant may include one or more openings to accommodate packing of bone graft material and/or to allow for bone ingrowth. In certain embodiments, one or more surfaces of an implant may include material, such as osteoconductive scaffolding, to enhance integration of the implant in a patient's spine. In certain embodiments, implants depicted herein may include features allowing the implant to provide a desired lordotic angle between vertebrae. A desirable lordotic angle can be between about 8 degrees to about 18 degrees. For example, the superior and/or inferior walls may optionally can include teeth, spikes, ridges or other projections (e.g., tapered projecting elements) that protrude perpendicular from the superior and/or inferior surfaces, such that deployment results in this or these element(s) extending into the adjacent endplate(s). That is, the projecting elements (e.g. spikes, teeth, etc.) from the superior and/or inferior walls may be designed to penetrate the respective superior and inferior endplates upon expansion of the device to further stabilize the device and mitigate implant migration.

FIGS. 1A-1D provide an illustration of an intervertebral device 100 according to some embodiments as the device is expanded from a fully collapsed (FIG. 1A) to a fully expanded/articulated (FIG. 1D) configuration. The intervertebral device 100 can include a posterior portion 102, an anterior portion 104 opposite from the posterior portion 102. The walls of the intervertebral device 100 can be generally trapezoidal, wherein the parallel segments of the trapezoidal walls are oriented such that the longer segment is anterior and the shorter segment is posterior. Each wall can be narrower posterior than anterior.

FIG. 1A illustrates an intervertebral device 100 with four walls or surfaces: a superior wall 22, inferior wall 24, and two lateral sidewalls 26. The superior wall 22 is opposite from the inferior wall 24, with a pair of sidewalls 26 between the superior wall 22 and inferior wall 24. The superior wall 22 and inferior wall 24 are the portions of intervertebral device 100 closest to the exposed ends of vertebral bodies when implant 100 is in implantation space. The superior wall 22 and inferior wall 24 may also be referred to as the cephalad surface and caudal surface, respectively. Superior (i.e. cephalad) 22, inferior (i.e. caudal) 24 and lateral sidewalls 26 can be hinged along their respective midlines. Each wall can be narrower posterior than anterior. The superior wall 22, inferior wall 24, and sidewalls 26 thus define an implant body having a cephalad surface, a caudal surface, and an internal fusion promotion cavity extending between.

Figure 11A:
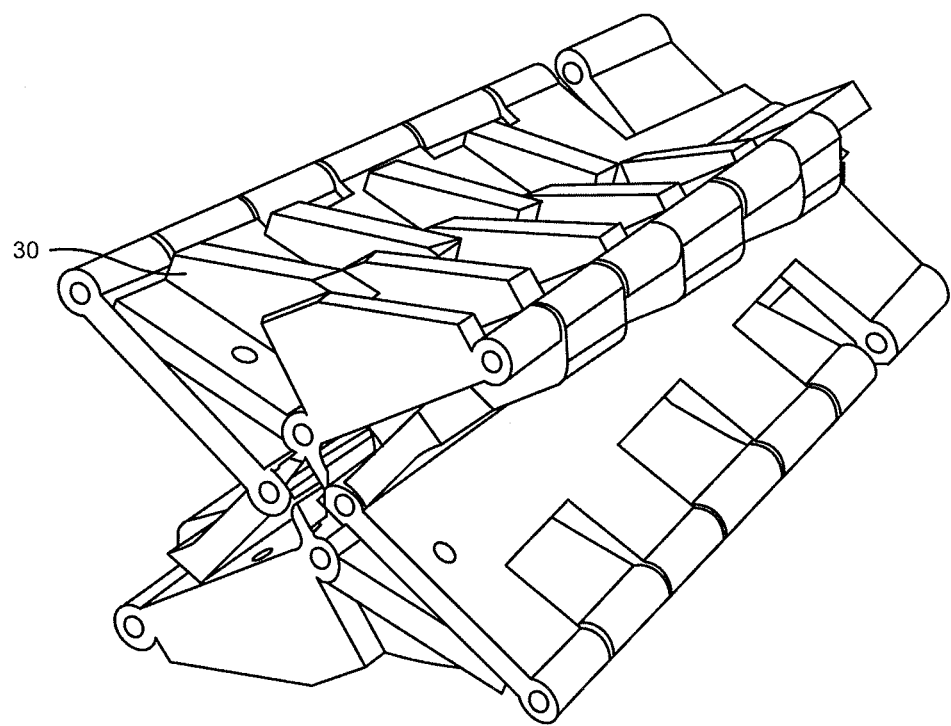
FIG. 11A provides a perspective view of another embodiment of an intervertebral device.
Figure 11B:
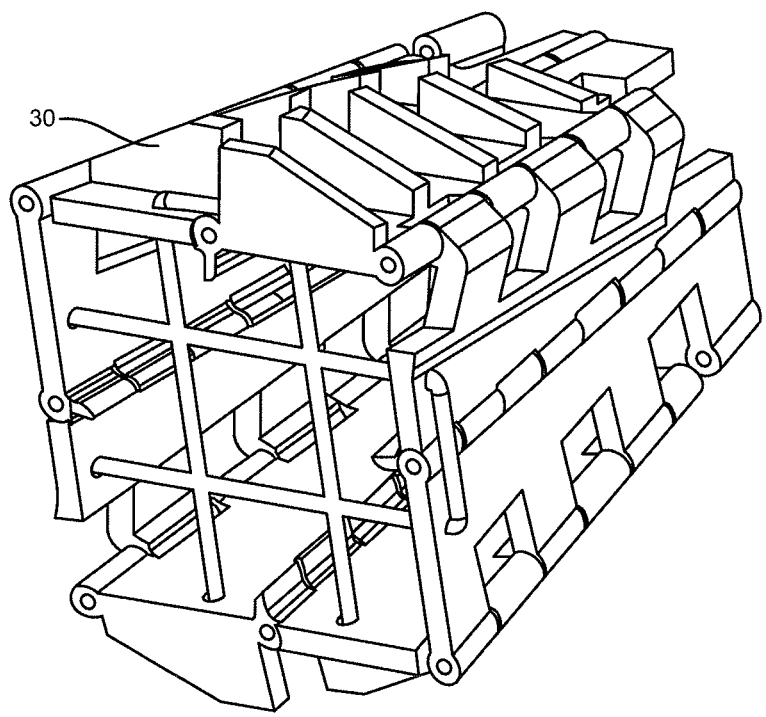
FIG. 11B provides a perspective view of the intervertebral device of FIG. 11A in an expanded configuration.

The superior and inferior walls 22, 24 may optionally include projecting elements 30. In some embodiments, the projecting elements 30 can be tapered and have a cone or spiked shape such that a sharpened distal end can penetrate one or more of the respective superior and inferior endplates and function to further stabilize the intervertebral device 100 and mitigate implant migration when in the fully expanded configuration. In another embodiment, the projecting elements 30 can have a blunt shape such that they do not penetrate the endplates. In another embodiment, the projecting elements 30 can have a wedge shape such that they provide additional "lift" against one or more of the vertebral endplates (see FIGS. 11A and 11B). It should be appreciated that the projecting elements 30 having this configuration can also penetrate the endplates at one or more regions of the wedge. The projecting elements 30 can also have an elongate shape and further include a texture or additional barb elements on their surface that can penetrate the endplates.

When the intervertebral device 100 is in the unexpanded configuration, the projecting elements 30 can be directed inward or toward the midline of each wall surface on which they are positioned such that the projecting elements 30 have a sub-flush configuration in the collapsed state and do not snag tissues during implantation. The projecting elements 30 upon expansion can extend beyond the outer perimeter of the peripheral walls such that they provide additional height or lift on the vertebrae or penetrate the vertebral endplates. In the embodiment shown in FIGS. 11A-11B, the projecting elements 30 provide a ribbed surface that prevents migration making the intervertebral device is less prone to slippage once implanted between the vertebrae.

It should be appreciated that the superior and inferior walls 22, 24 can have apertures, through-holes or other features providing for an open architecture between the projecting elements 30 such that bone growth material or other material inserted within the interior volume of the device can penetrate the walls and contact the vertebral endplates for promotion of bone fusion.

The projecting elements 30 can also be positioned on one or more of the opposing sidewalls 26. The projecting elements 30 positioned on the sidewalls 26 can provide additional stiffness and enhance wall bearing stability. The opposing sidewalls 26 can increase the thickness of the walls in the regions where the projecting elements 30 are positioned and prevent buckling of the walls upon application of a load.

Figure 8A:
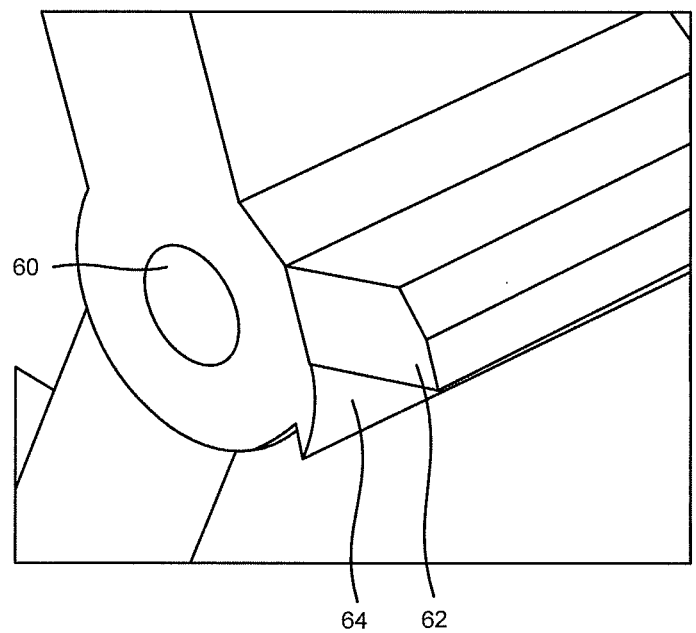
FIGS. 8A to 8C provide a detailed view of the hinge mechanism of an intervertebral device of the present embodiments and related elements (e.g., ridge and overhang).
Figure 8B:
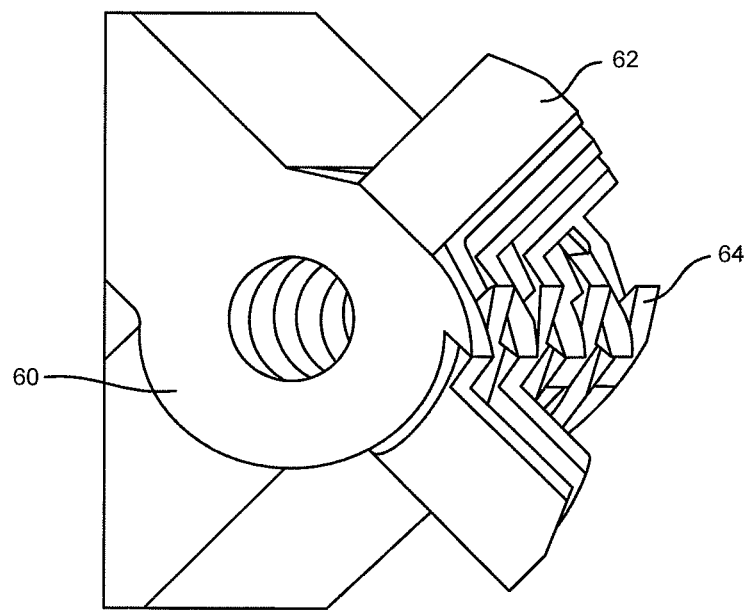
Figure 8C:
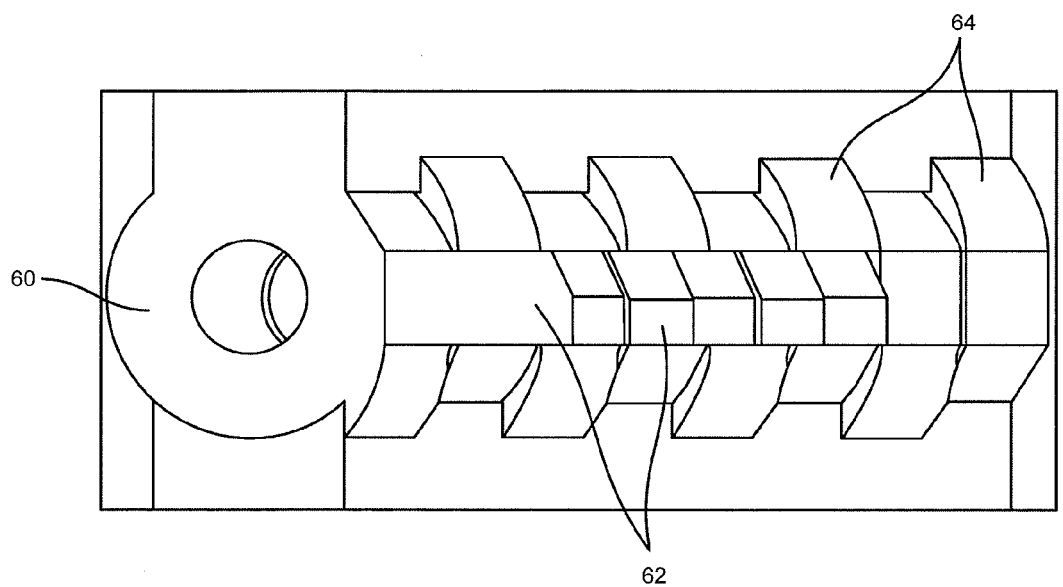

The superior wall 22 and inferior wall 24 can each mate with the two lateral walls 26 at a joint having a rotatable hinge arrangement. The hinge arrangement can include a plurality of interlocking hinge elements 60. The hinge arrangement may include block elements 40 that give way to openings or apertures 42 when the device is rotated around the joint and expanded from a collapsed to an expanded configuration (see FIG. 1D). The block elements 40 can allow for material implanted within the interior volume to exit the device 100 and make contact with the vertebral endplates. The hinge arrangement can further include a plurality of ridge elements 62 and overhangs 64 (see FIG. 8A to 8C). Depending on the position of the ridge elements 62 and overhangs 64, expansion of the device 100 can vary. The overhangs 64 can be configured to allow for hypo-extension, hyper-extension or on center extension of the wall elements. For example, the overhangs 64 can be configured relative to the hinge element 60 to prevent (or allow) over-expansion or over-extension around the hinge. In an embodiment, the overhangs 64 can be configured to allow over-expansion such that one or more of the walls has an A-frame type architecture. In another embodiment, the overhangs 64 can be configured to allow under-expansion such that one or more of the walls has a V-frame type architecture. In another embodiment, the overhangs 64 can be configured to allow on center expansion such that one or more of the walls has a parallel arrangement (see FIG. 8C).

Figure 1C:
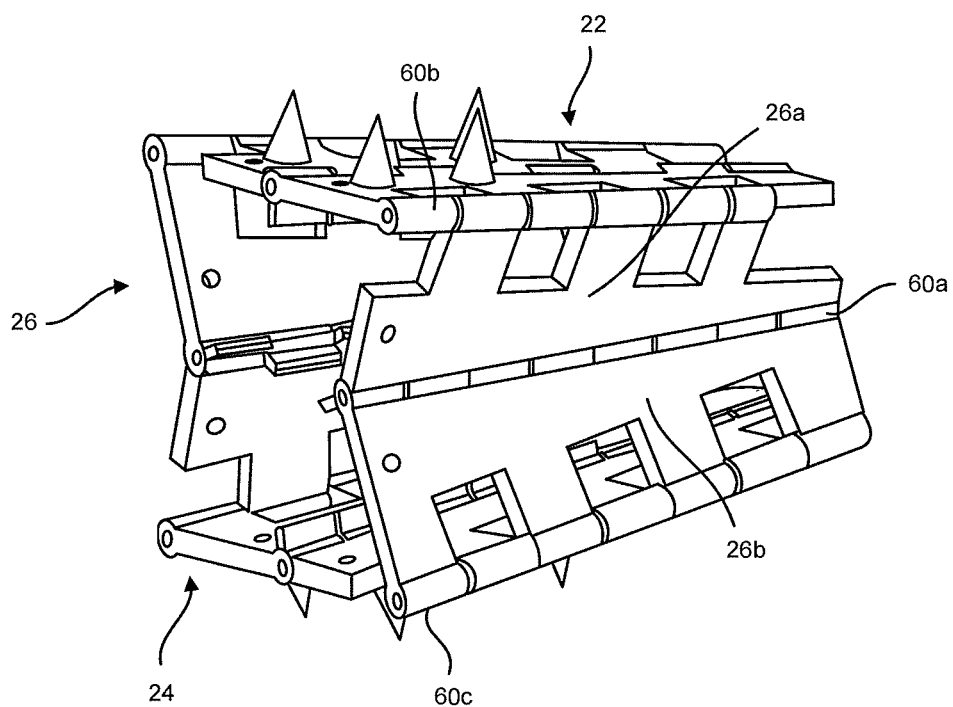
Figure 1D:
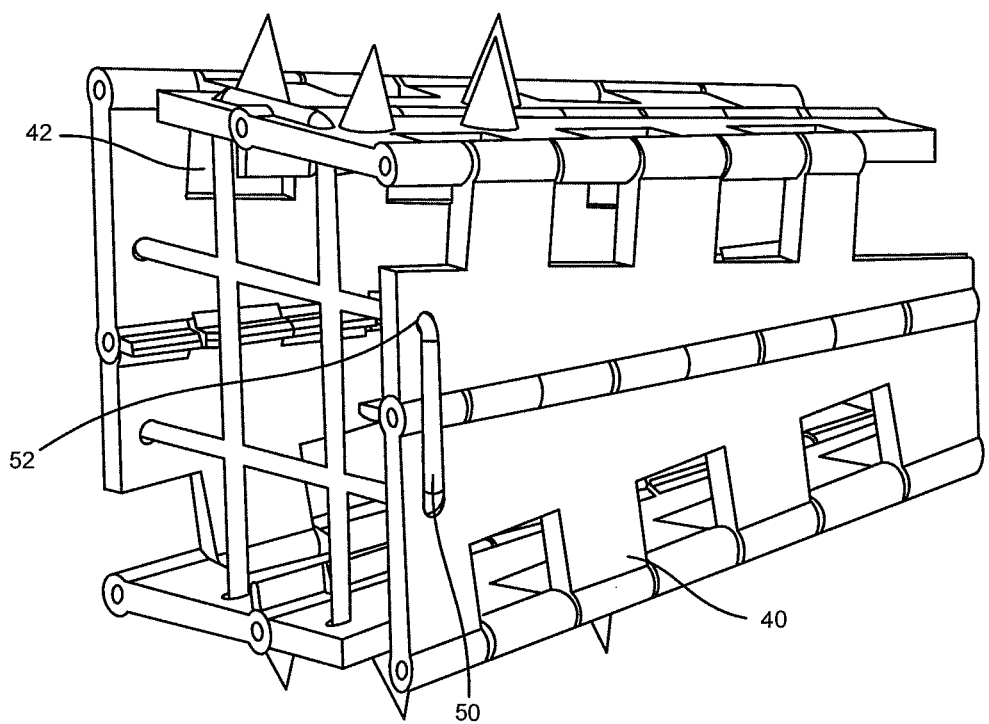
Figure 2A:
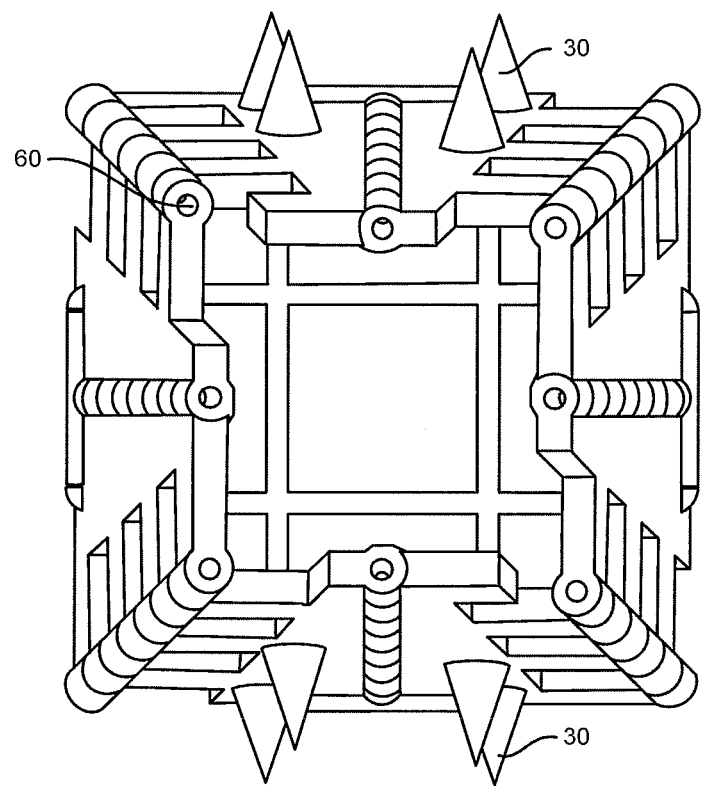
FIG. 2A provides a detailed view of the posterior end an intervertebral device of the present embodiments in the fully expanded configuration.
Figure 2B:
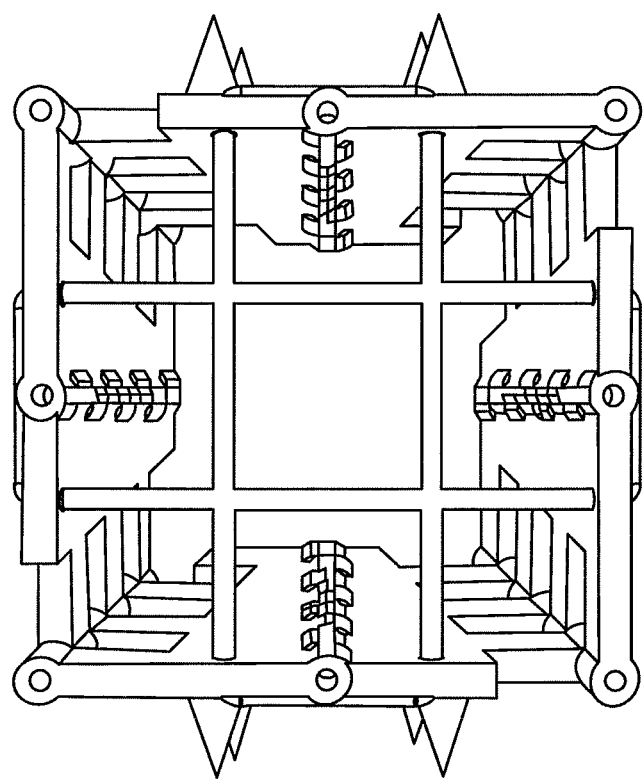
FIG. 2B provides a detailed view of the anterior end an intervertebral device of the present embodiments in the fully expanded configuration.
Figure 2C:
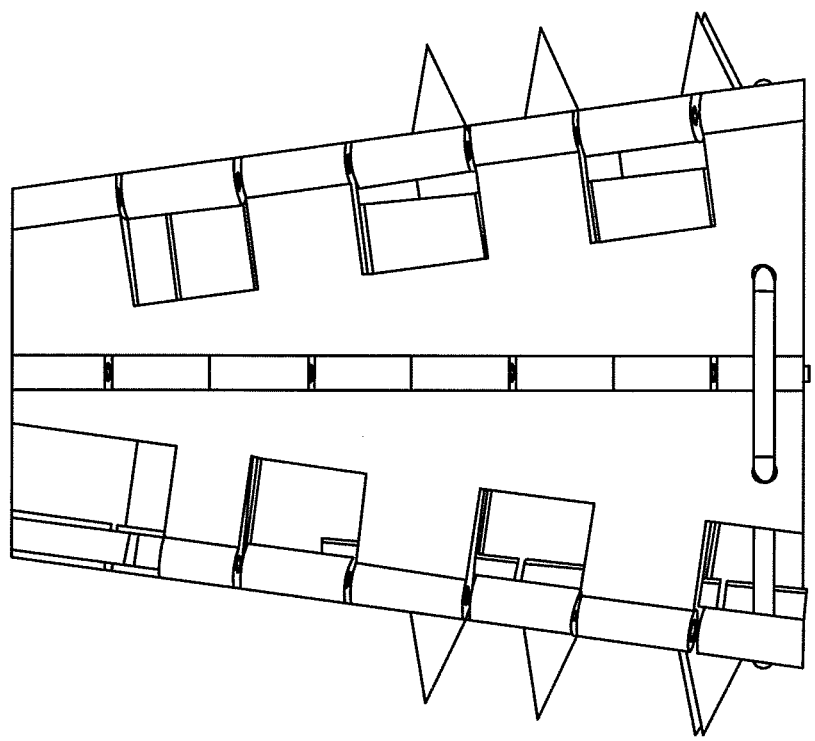
FIG. 2C provides a detailed view from the lateral side of an intervertebral device of the present embodiments in the fully expanded configuration.
Figure 3A:
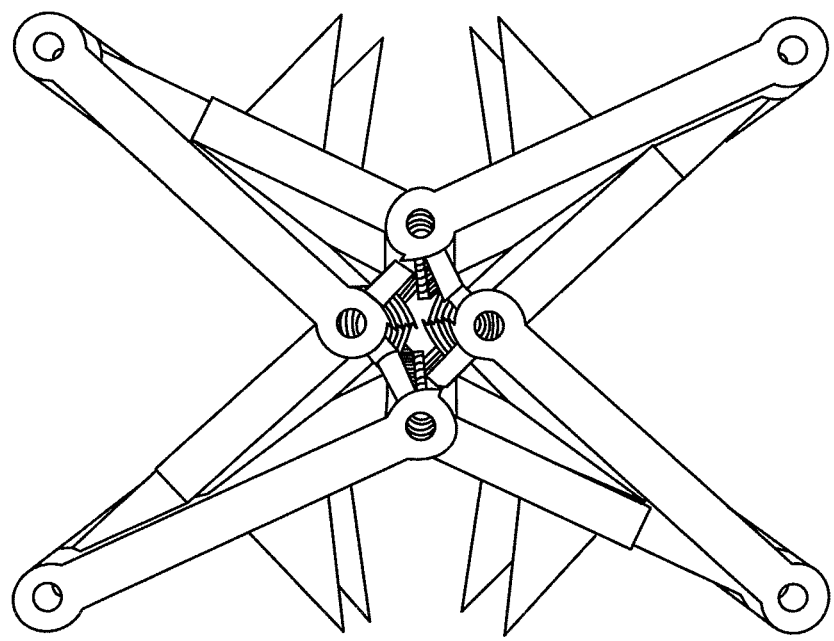
FIG. 3A provides a detailed view of the anterior end an intervertebral device of the present embodiments in the fully collapsed configuration.
Figure 3B:
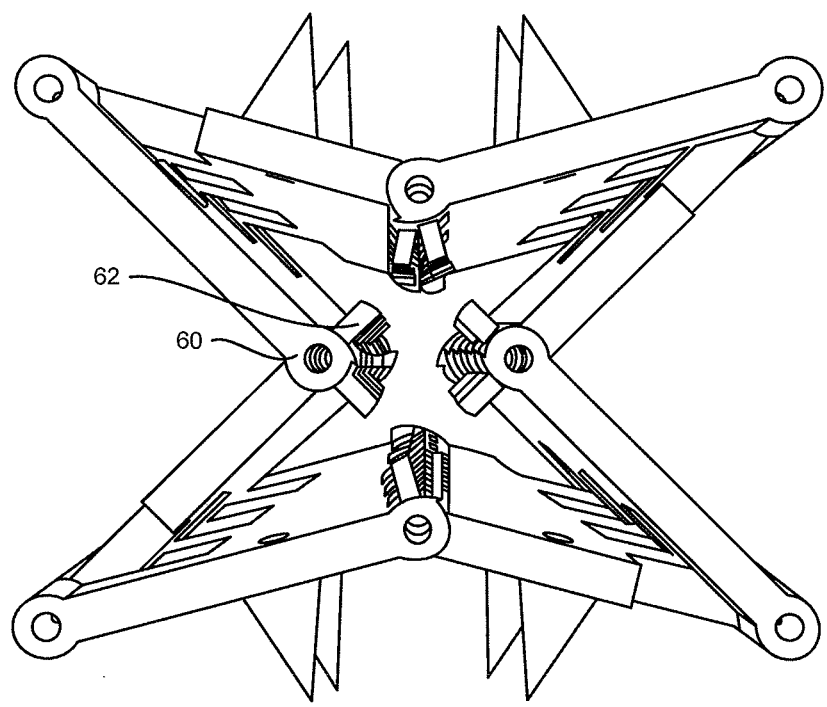
FIG. 3B provides a detailed view of the anterior end an intervertebral device of the present embodiments in a slightly expanded configuration.
Figure 3C:
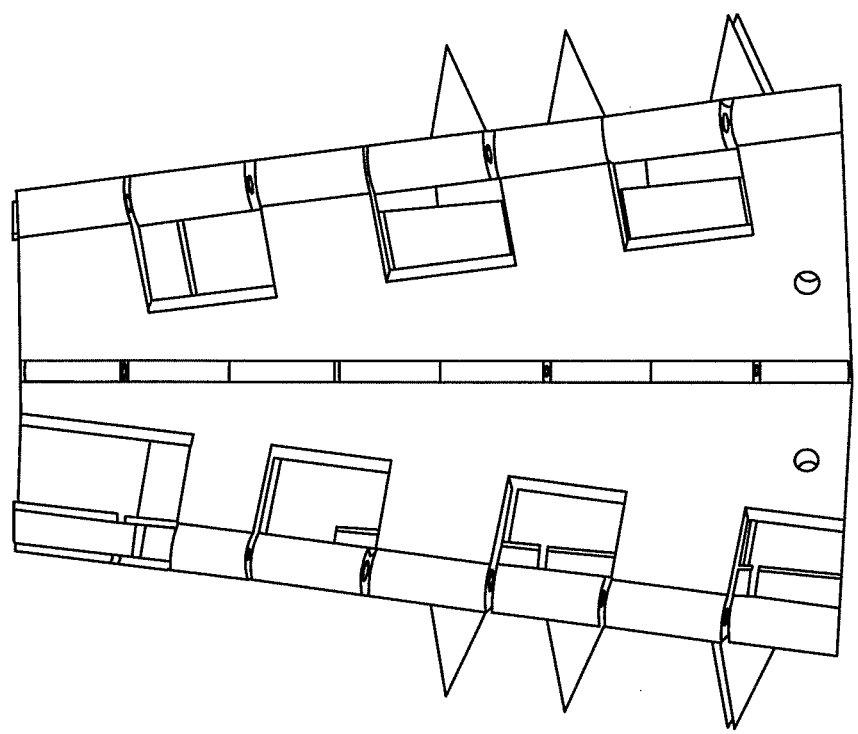
FIG. 3C provides a detailed view from the lateral side of an intervertebral device of the present embodiments in the fully collapsed configuration.

One or more of the superior wall 22, inferior wall 24, and two lateral sidewalls 26 can be monolithic. The one or more of the superior wall 22, inferior wall 24, and two lateral sidewalls 26 can also include two or more wall portions that articulate relative to one another. As best shown in FIG. 1C, the lateral sidewalls 26 can each include a superior plate element 26a coupled by an internal hinge mechanism 60a to an inferior plate element 26b. The axis of the internal hinge mechanism 60a can be coplanar with the midline of the device. Further, the axis of the internal hinge mechanism 60a of one lateral sidewall 26 can be coplanar with the axis of the internal hinge mechanism 60a of the opposing lateral sidewall 26 just as the axis of the internal hinge mechanism 60a of the superior wall 22 can be coplanar with the axis of the internal hinge mechanism 60a of the inferior wall 24. The axis of the internal hinge mechanism 60a can be non-parallel to the axis of the hinge mechanism 60b that couples the superior plate element 26a of the lateral sidewall 26 to the superior wall 22. Further, the axis of the internal hinge mechanism 60a can be also non-parallel to the axis of the hinge mechanism 60c that couples the inferior plate element 26b of the lateral sidewall 26 to the inferior wall 24. The device, in turn, can include bifurcated, hinged monolithic sidewalls having a trapezoidal shape such that the hinge axes are coplanar with the midline of the device, but non-parallel to each other.

When the device 100 is fully expanded, the ridge elements 62 can line up to form a linear track. In some embodiments, the linear track formed by the ridge elements 62 extends from the anterior end 102 and partially towards the posterior end 104 of the intervertebral device 100 (e.g., 20% to 80% of the length of the device). The portion of the fully expanded intervertebral device 100 absent the linear track can be configured to contact the wedge portion 220 of the brace 200, discussed in detail herein. The portion of the fully expanded intervertebral device 100 having the linear track can be configured to contact the flange 232 of the second segment of the wedge portion 230 of the brace 200, discussed in detail herein.

The intervertebral device 100 may further include small openings or suture holes 52 for receiving respective ends of a tether 50 (e.g., suture, thread, cable, braid, metallic filaments, and the like). The holes 52 can extend completely through one or more of the walls of the intervertebral device 100 and can be configured for receiving respective ends of tether 50. The tether 50 may be incorporated into the intervertebral device 100 prior to, during or after implantation. The tether 50 can be loose in the pre-deployed or collapsed state and become taut in the deployed or expanded configuration of the intervertebral device 100. The tether 50 may also be configured to stabilize the intervertebral device 100 or block the fill material delivered to the cavity of the expanded intervertebral device 100 from oozing out.

Figure 12A:
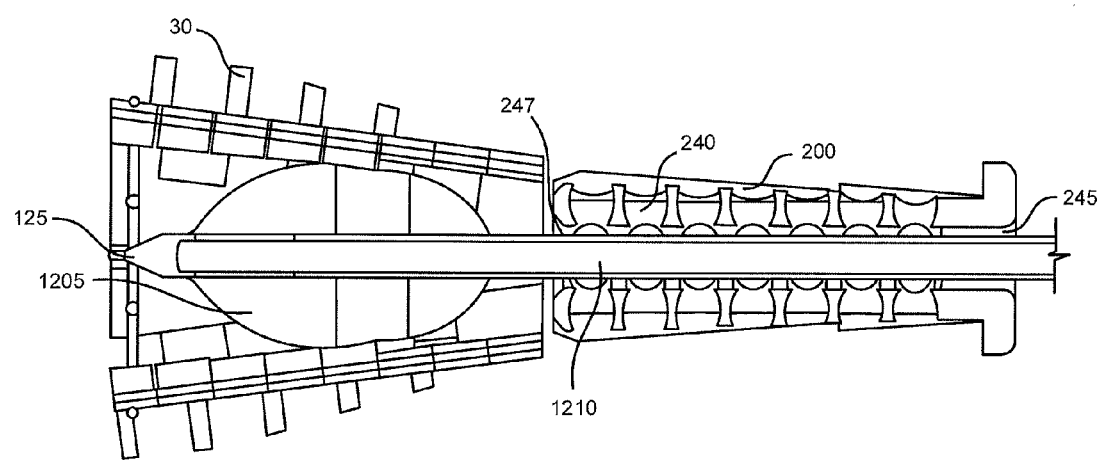
FIG. 12A provides a side, cross-sectional view of an embodiment of an intervertebral device in an expanded configuration.
Figure 12B:
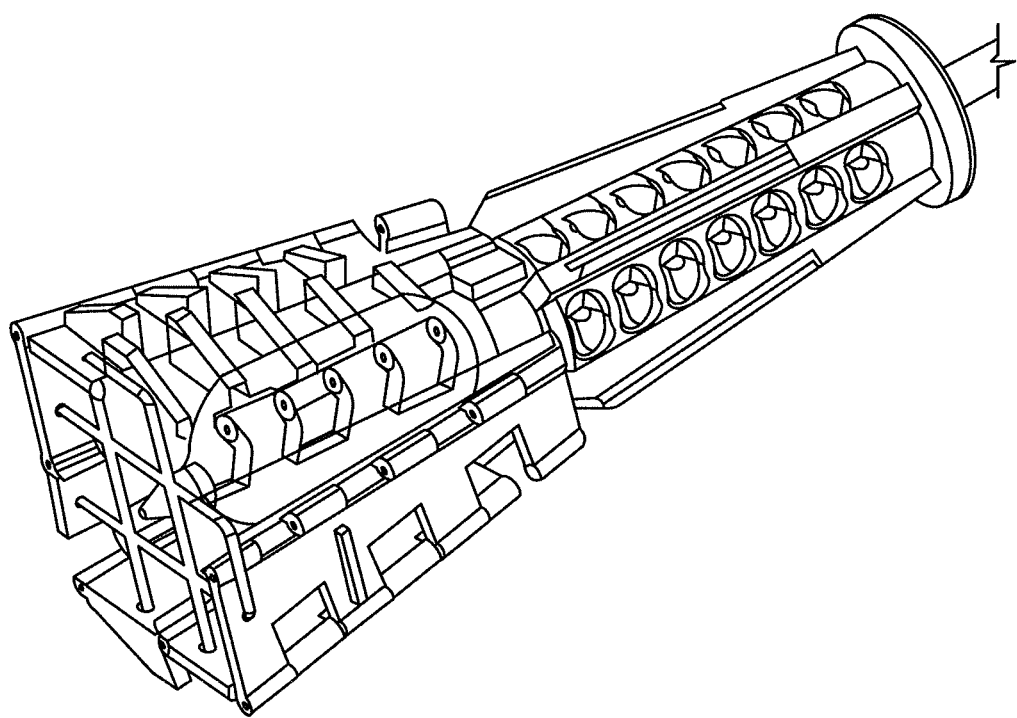
FIG. 12B provides a perspective, cut-away view of the intervertebral device of FIG. 12A.

The device may be expanded in situ. Various methods for in situ expansion are considered herein. In one embodiment, mechanical distraction using a wedging tool to pry the walls apart or an articulating tool that pushes or pulls opposing walls apart is considered. In some embodiments, an obturator can be used. The obturator can have a tapered end that fits into an entry port of the collapsed intervertebral device 100 and an outer diameter that can force the walls of the intervertebral device 100 outward into at least a partially expanded configuration. The outer diameter of the obturator can be between about 6 mm to about 7 mm, although smaller and larger outer diameters are considered herein. In other embodiments, in situ expansion can be performed using hydraulic expansion such as with an expandable element such as an elastomeric balloon (see FIGS. 12A-12B), as will be discussed in more detail below.

Once fully expanded, the intervertebral device 100 may be further stabilized with a cylindrical brace 200 (see e.g., FIGS. 4A to 4E). The brace 200 can support the intervertebral device 100 under load. In some embodiments, the brace 200 slides from posterior 102 to anterior 104, while locking on the opposing four walls 20 adjacent to the hinge mechanism 60, via relatively linear tracks that employ some form of undercut geometry. In some embodiments, the linear tracks are formed by the ridge elements 62 positioned on the hinge mechanism 60.

In some embodiments, the brace can include a detent mechanism, a shank 202 and posterior cap 210. The brace 200 may be of identical length to that of the intervertebral device 100, or slightly smaller (e.g., 0.2 mm to 5 mm shorter). The brace 200 is designed to match the geometry of the cavity created by the full expansion of the intervertebral device 100. In some embodiments, the brace 200 is cylindrical having a diameter that expands conically when progressing from the posterior end to the anterior end in a manner that corresponds to the geometry of the interior of the intervertebral device 100. The brace 200 may further include a plurality of wedge locking elements 220 and/or a plurality of bore holes 240.

The plurality of bore holes 240 may be pre-filled with a material, such as a bone growth material, or filled after implantation. In some embodiments, the bore holes 240 and/or openings accommodate packing of bone graft material and/or to allow for bone in-growth. In certain embodiments, one or more surfaces of an implant may include material, such as osteoconductive scaffolding, to enhance integration of the implant in a patient's spine. The bore holes 240 can extend through one or more walls of the brace 200, such as in a caudal-cephalad orientation as well as a medial-lateral orientation. The brace 200 can also be cannulated and include a central bore 245 extending along its longitudinal axis for insertion of materials and/or devices through the brace 200 (see FIGS. 12A-12B) as will be discussed in more detail below.

The top of the posterior cap 210 may include a cap screw 250 such as a hex, slot, or square nut for use in the mechanical rotation of the brace 200 (see e.g., 6A to 6E). The posterior cap or wall 210 may be associated with the brace 200 or may be independently associated with the expanded device 100, to further stabilize the walls and to obstruct material from displacing from the interior of the device via the posterior portal. This posterior cap or wall may be locked to the perimeter walls with mating interior and/or exterior geometries, with or without a screw lock and detent mechanism.

In some embodiments, the posterior cap 210 has a geometry that is designed to stop the advancement of the brace 200 into the intervertebral device 100. In some embodiments, the cap 210 is round and of a diameter larger than the opening at the posterior 102 of the intervertebral device 100. For example, FIGS. 4A to 4E and FIGS. 5A to 5E provide different views illustrating the advance of the brace 200 into the cavity created by the full expansion of the intervertebral device 100. These figures show that the brace 200 can be advanced into the interior of the intervertebral device 100 until progress is halted by the engagement of the cap 210 and posterior end 102 of the intervertebral device 100.

Figure 4A:
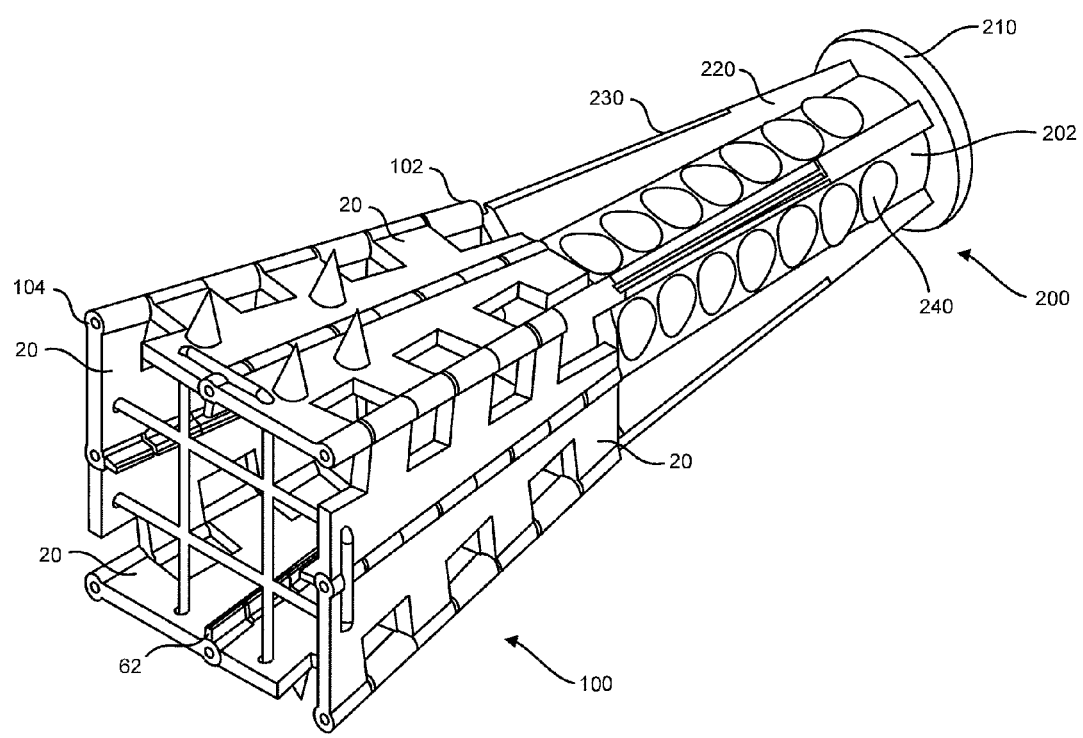
FIGS. 4A to 4E provides a perspective view of an intervertebral device and support brace of the present embodiments as the brace is inserted into the interior of an intervertebral device and rotated into a locked position.
Figure 4B:
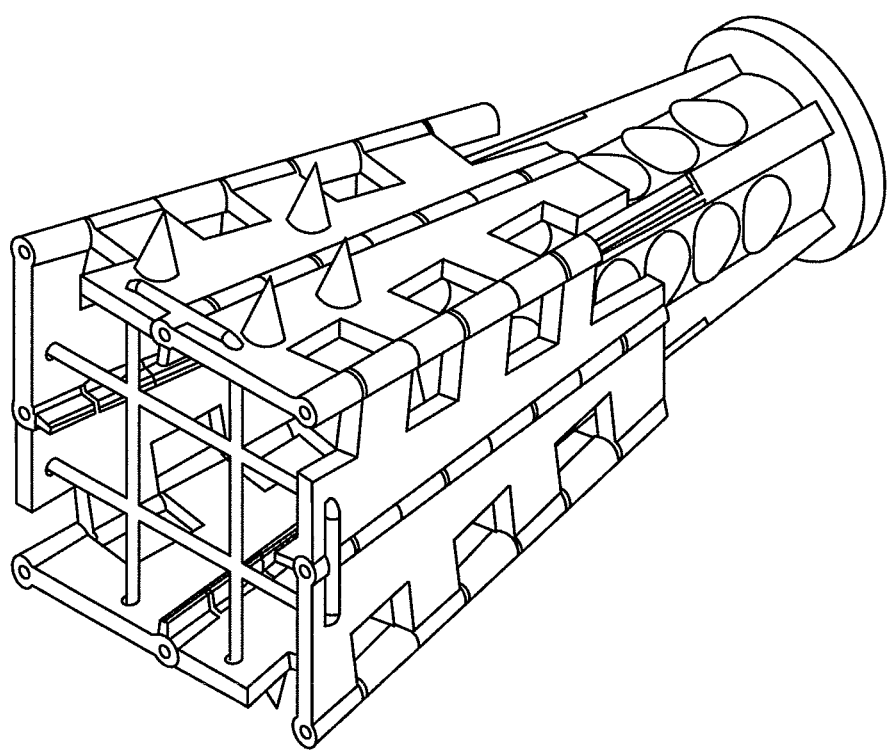
Figure 4C:
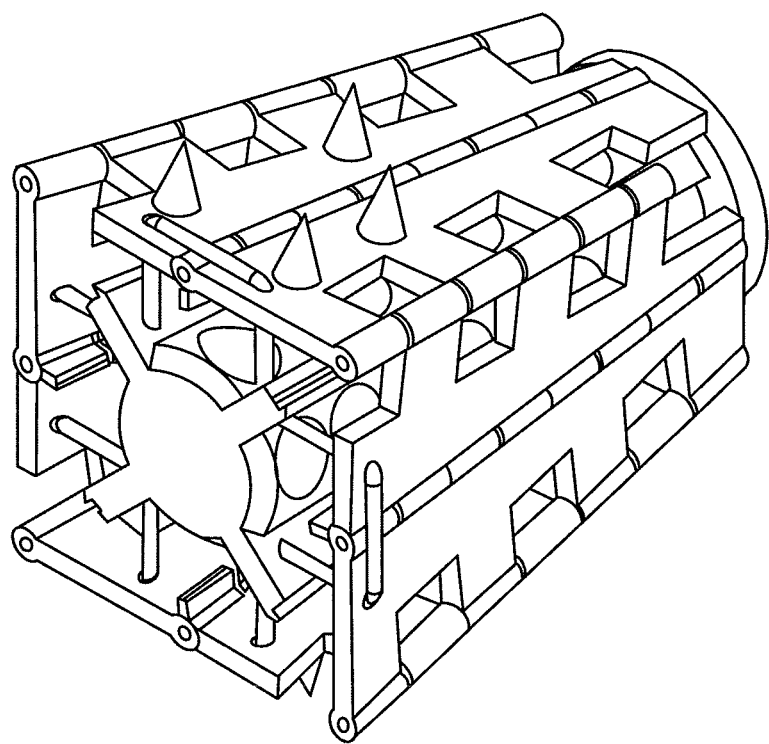
Figure 4D:
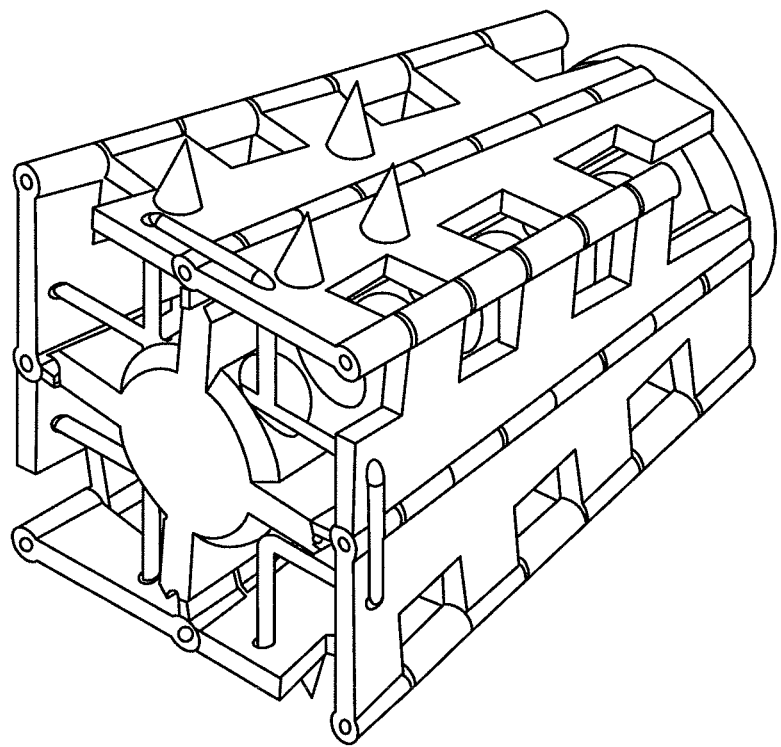
Figure 4E:
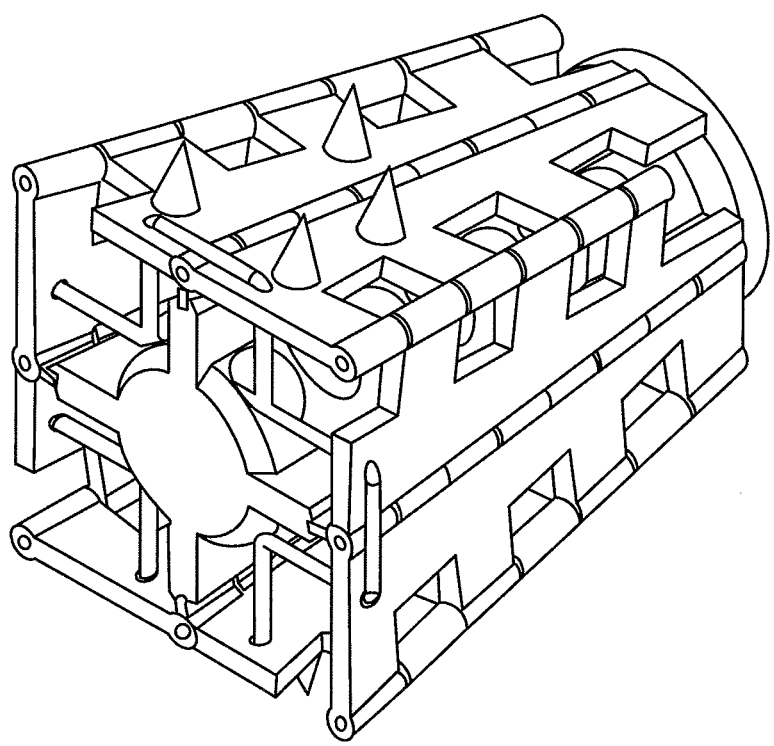
Figure 5A:
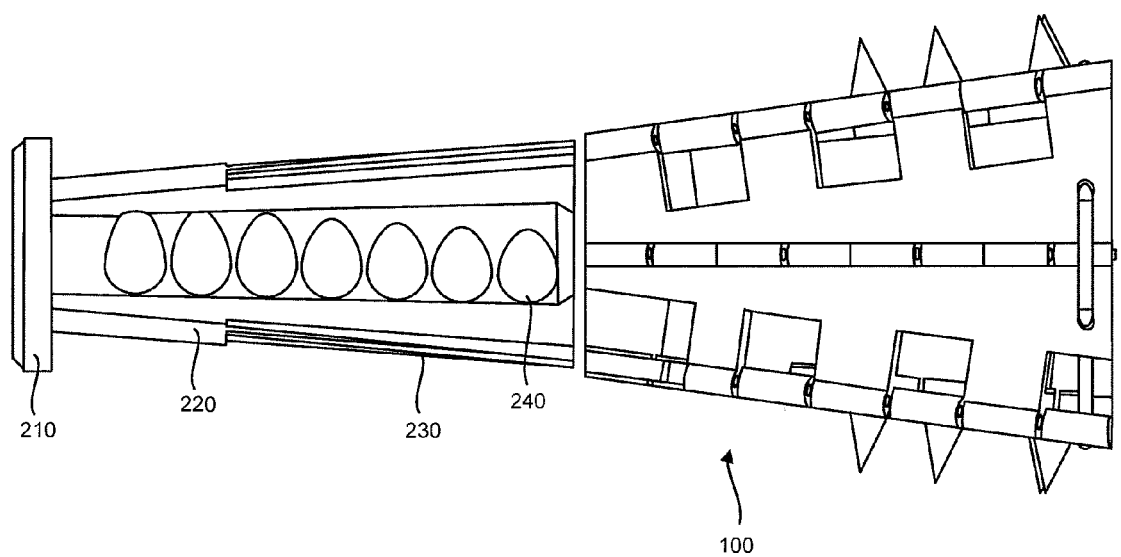
FIGS. 5A to 5E provides a side view of an intervertebral device and support brace of the present embodiments as the brace is inserted into the interior of an intervertebral device and rotated into a locked position.
Figure 5B:
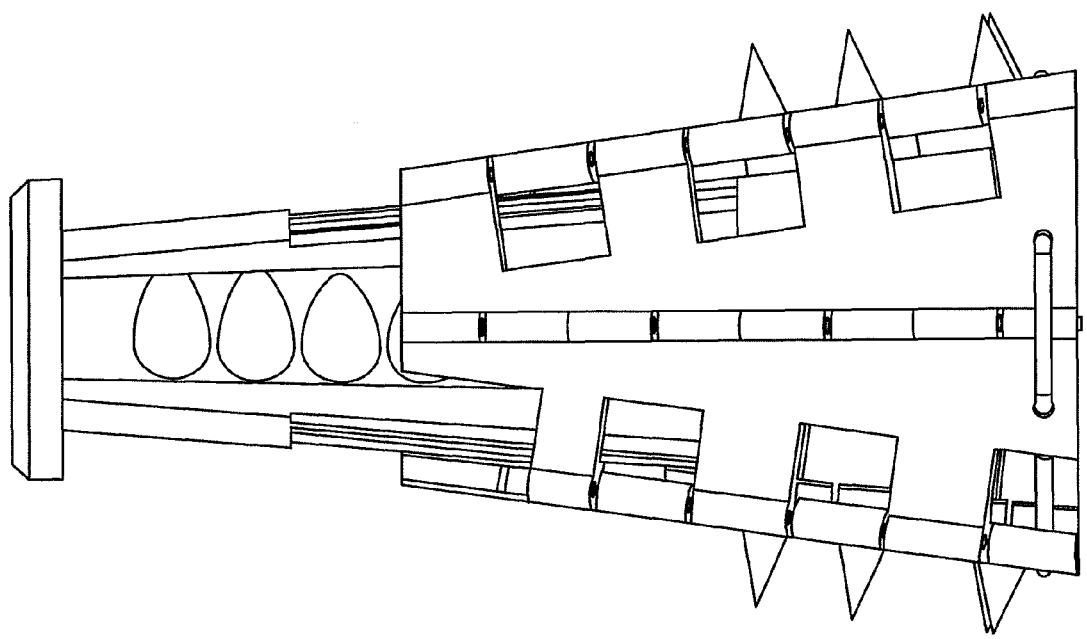
Figure 5C:
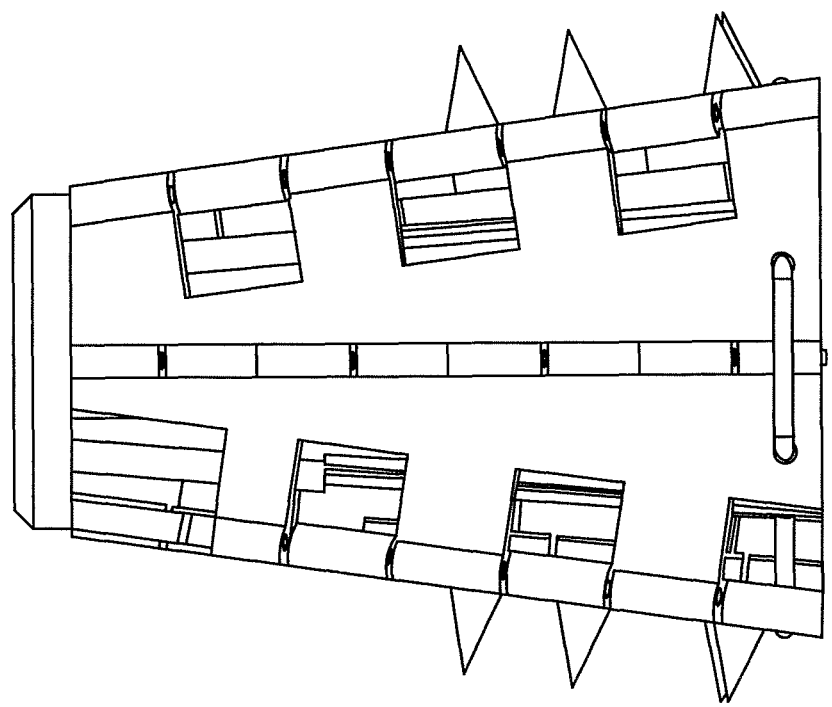
Figure 5D:
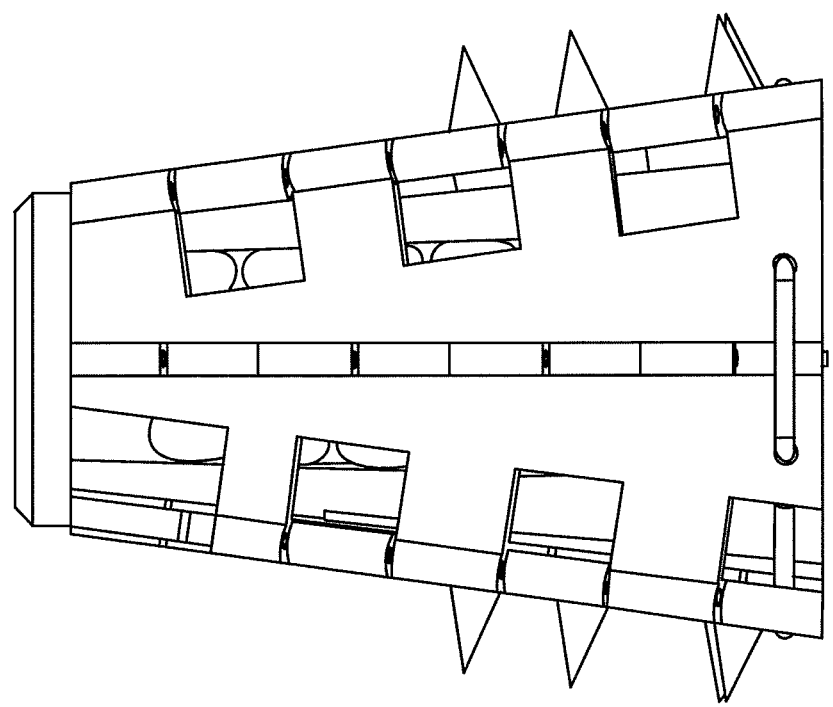
Figure 5E:
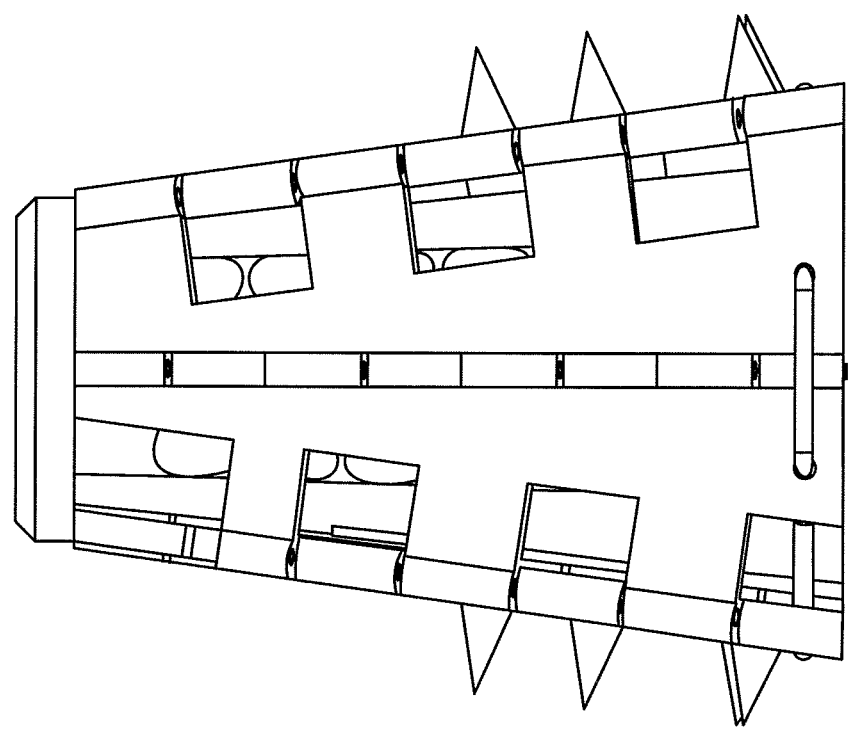
Figure 6A:
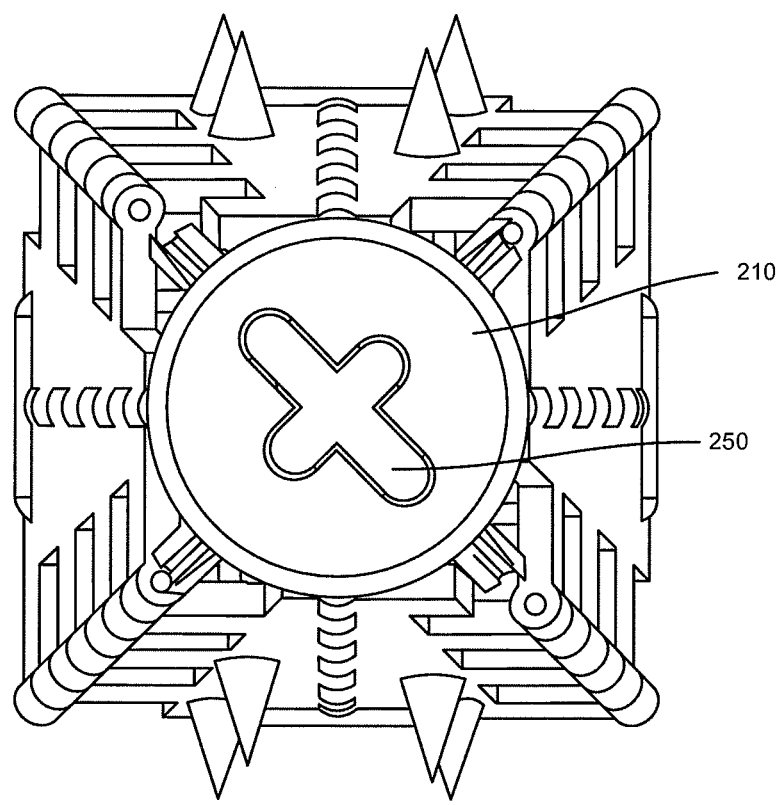
FIGS. 6A to 6E provides a posterior view of an intervertebral device and support brace of the present embodiments as the brace is inserted into the interior of an intervertebral device and rotated into a locked position.
Figure 6B:
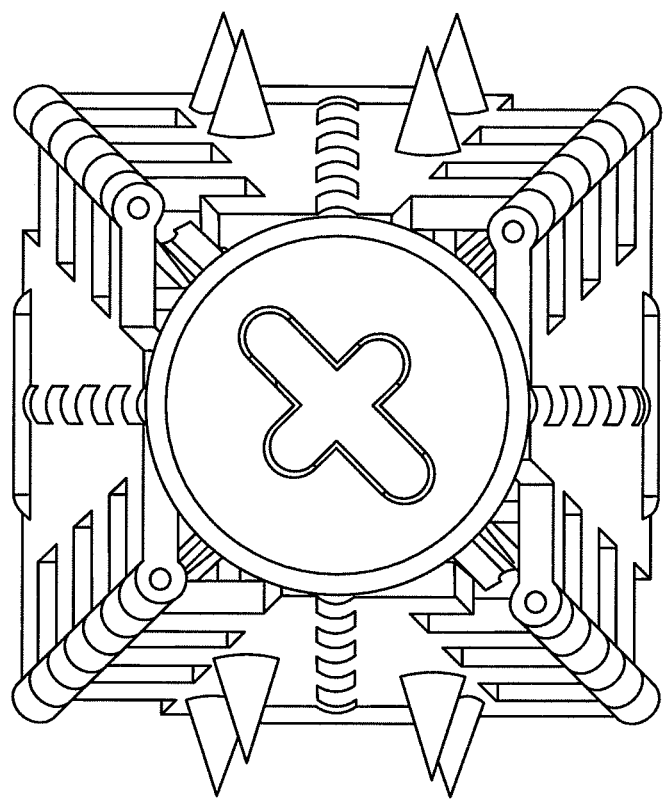
Figure 6C:
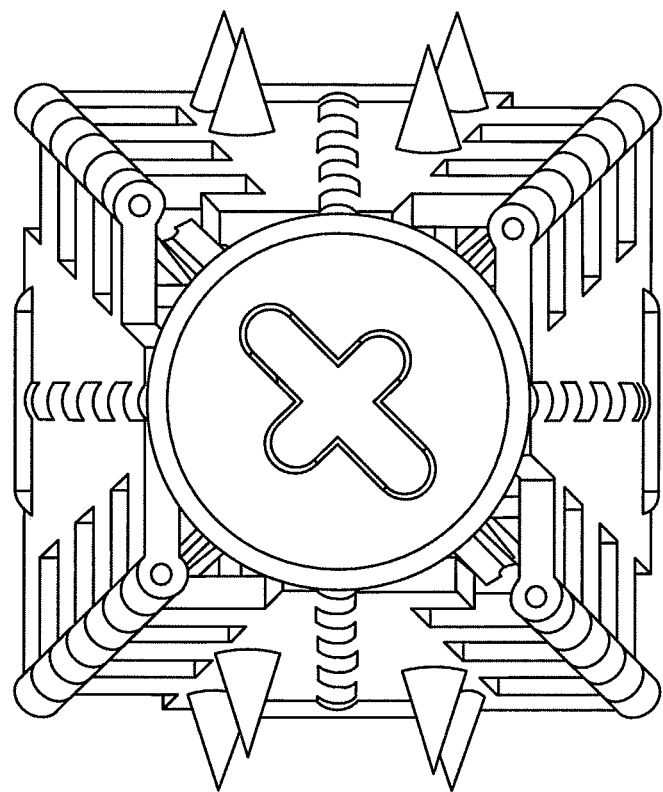
Figure 6D:
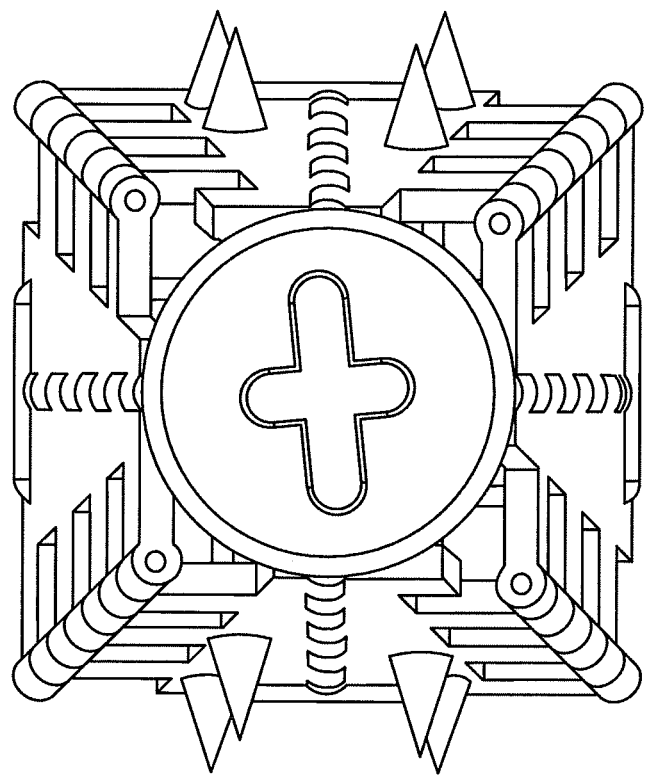
Figure 6E:
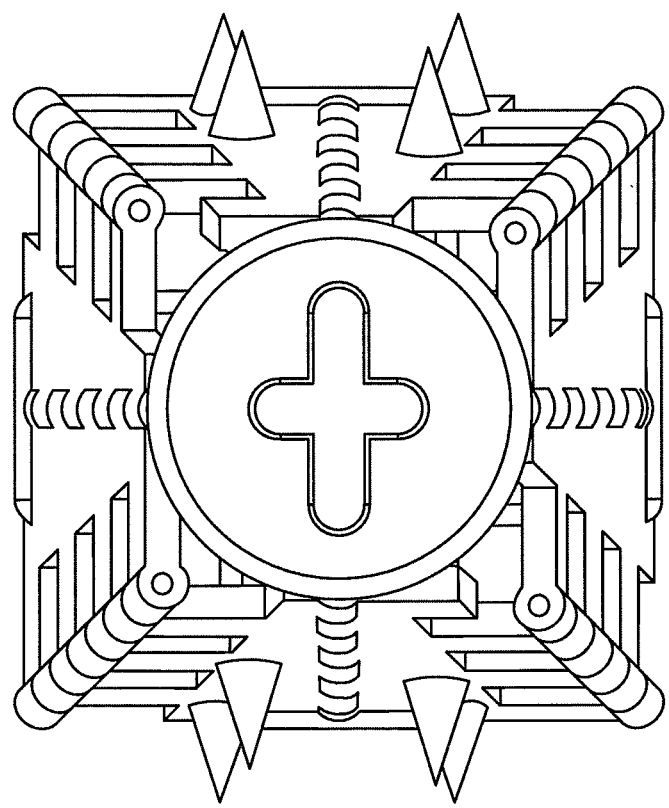
Figure 7A:
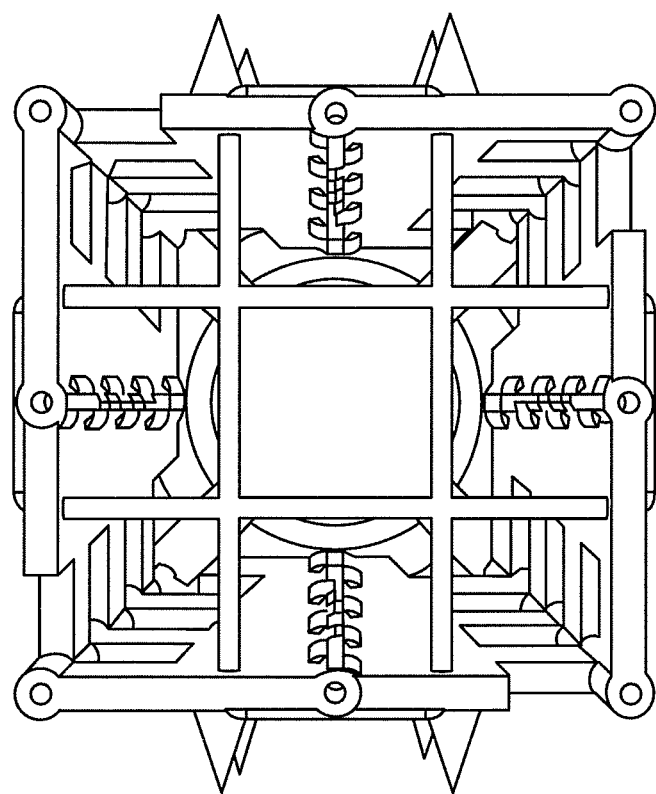
FIGS. 7A to 7E provides an anterior view of an intervertebral device and support brace of the present embodiments as the brace is inserted into the interior of an intervertebral device and rotated into a locked position.
Figure 7B:
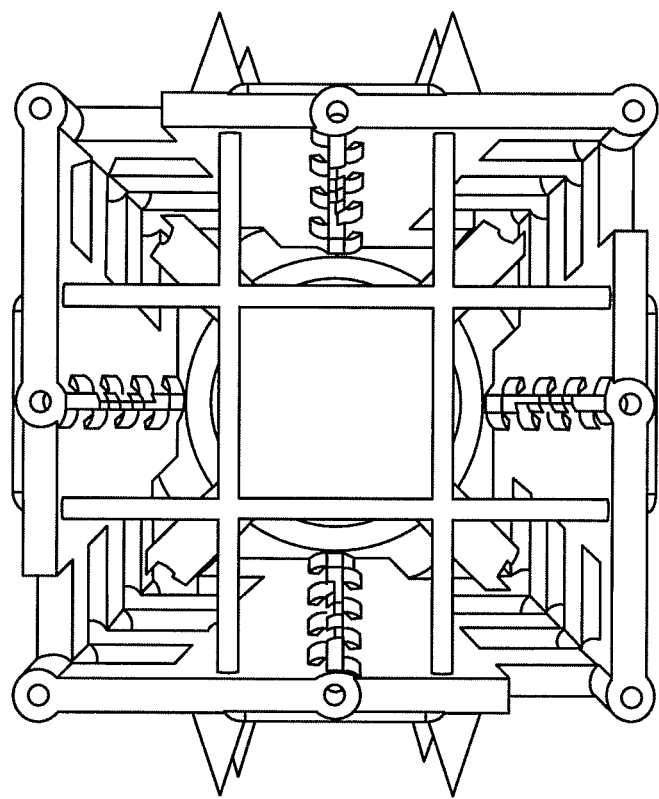
Figure 7C:
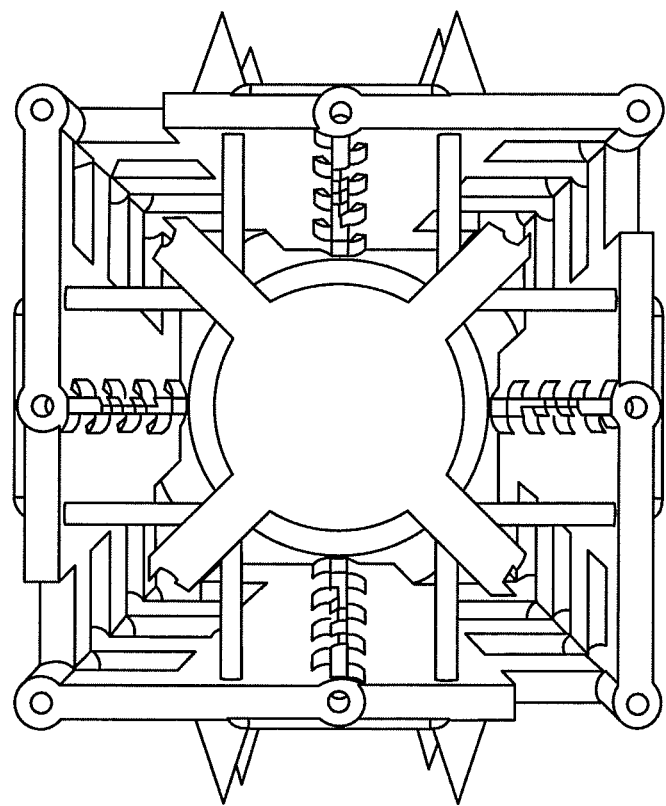
Figure 7D:
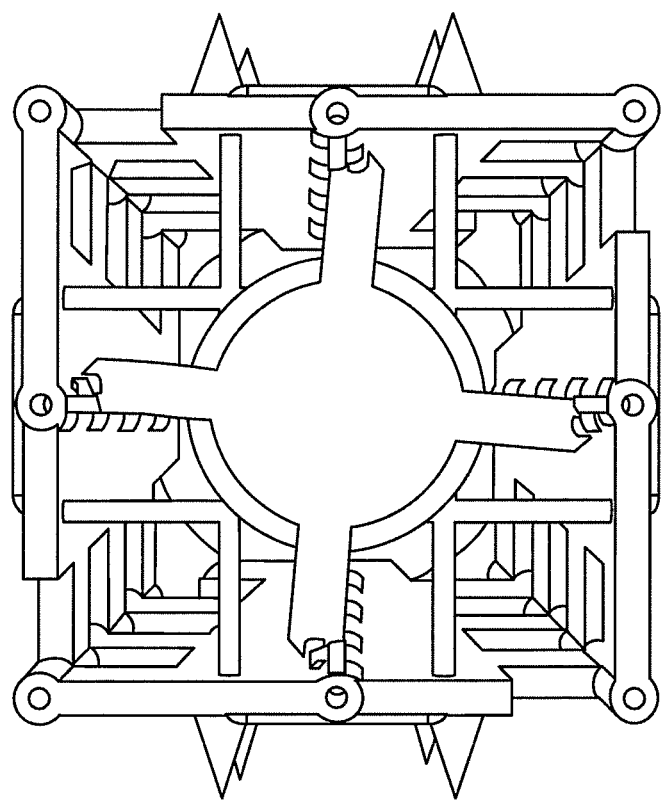
Figure 7E:
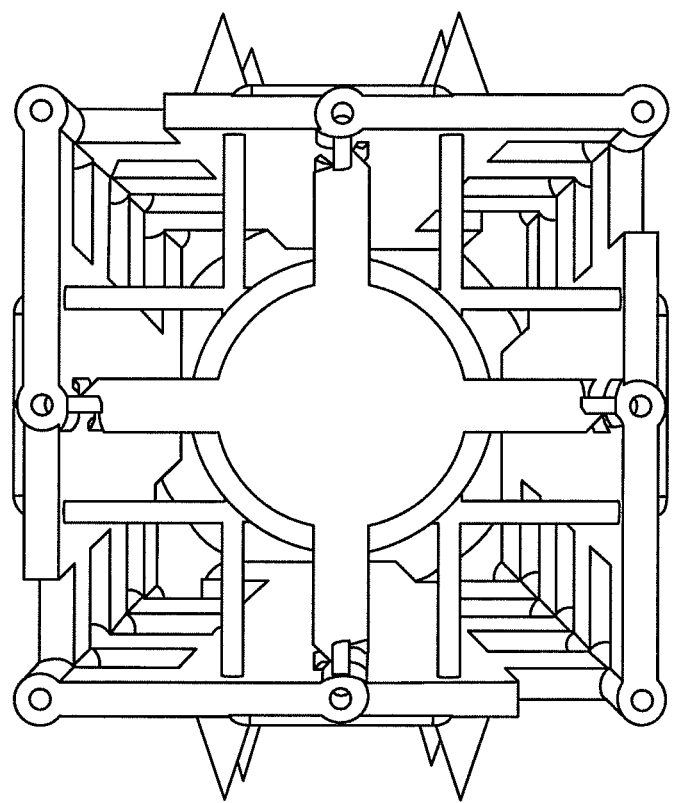

This bottoming out of the brace 200 indicates that the brace 200 is ready to be locked into position, which may be accomplished via rotation of the brace 200 and deployment of a detent mechanism. In some embodiments, the brace 200 is locked into position by the engagement of the wedge locking body 220 with the walls of the intervertebral device 100. FIGS. 4A and 5A illustrate a wedge locking body 220 according to some embodiments. In some embodiments, the brace 200 has a first internal diameter that forms the shank 202. The shank 202 may expand conically from the posterior to the anterior of the brace 200 or may have a single diameter from the posterior to the anterior of the brace 200. In some embodiments, the brace 200 additionally has a second diameter, which is defined by the area taken by the plurality of wedge locking body elements 220 that protrude from the shank 202. The diameter of the plurality of wedge locking body elements 220 may expand conically from the posterior to the anterior of the brace 200 or may have a single diameter from the posterior to the anterior of the brace 200. In this regard, the diameter of the shank 202 and diameter associated with the wedge elements 220 expand conically from the posterior to the anterior of the brace 200 in a manner that corresponds to the tapering of the intervertebral device 100. The outer surfaces of the wedge elements 220 are generally configured to match the contour of the interior walls of the intervertebral device 100. In some embodiments, the wedge elements 220 are integrally joined to the shank 202 and may have a right-angled shape.

In some embodiments, the brace includes four wedge elements 220 that together form a cruciform, which functions to further stabilize the walls and to obstruct material from displacing/egressing from the interior of the device via the posterior portal. In some embodiments the cruciform provides support along the midlines of the walls 22, 24, 26 of the intervertebral device 100.

The brace 200 may be inserted into the intervertebral device 100 such that the wedge elements 220 are angled to the corners of the intervertebral device 100 such that the brace freely slides into the interior of the intervertebral device 100 (see e.g., FIGS. 4 and 5). The brace 200 can advance until movement is halted by the posterior cap 210. The brace can then be rotated (clockwise or counterclockwise as appropriate) into a locked position guided by the wedge elements 220. The wedge elements 220 can be integrally joined to the shank 202 and may have a right-angled shape. The brace 200 can be rotated such that the wedge elements 220 engage the walls of the intervertebral device 100. When the outer surfaces of the wedge elements fully engage the walls of the intervertebral device 100, the free sliding motion of the brace 200 can give way to the wedging action created by the force created between the walls of the intervertebral device 100 and the wedging elements 220 of the brace. The brace 200 can be formed of a variety of materials including, but not limited to PEEK or carbon fiber composite. The material can be selected to minimize the effect of radiodense material obstructing X-ray visualization of the interbody bone or graft consolidation.

Figure 9:
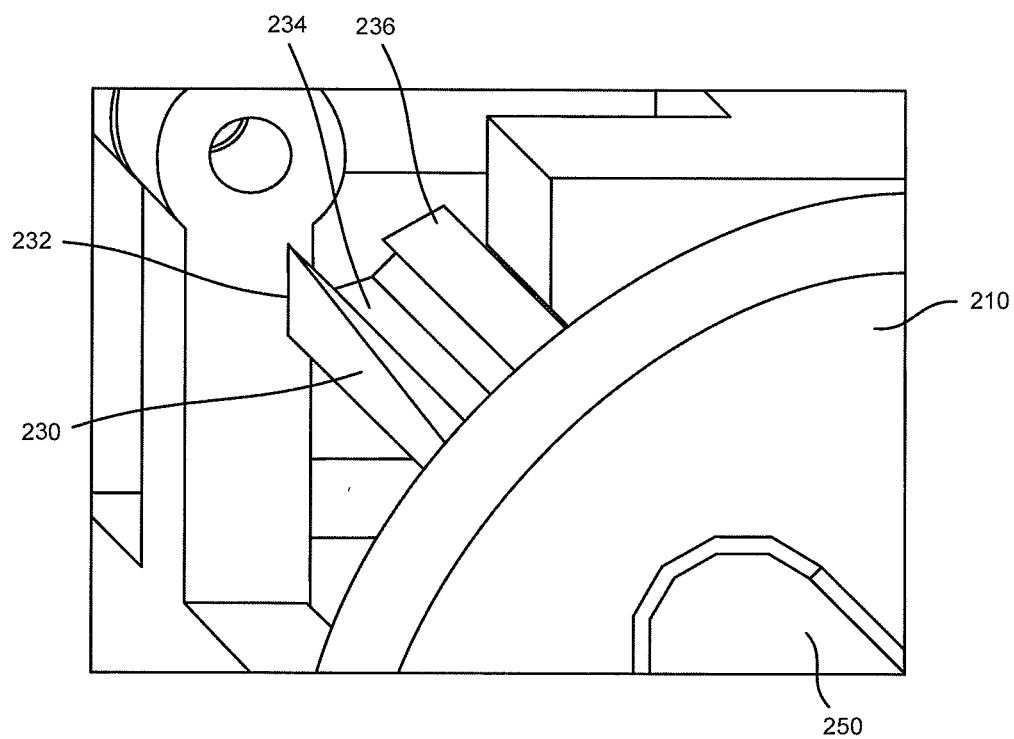
FIG. 9 provides a top view of a support brace of the present embodiments showing detail on the design of the anterior end of the wedge element comprising the features of a flange, groove and lock as the diameter of the wedge element extends past the diameter of the brace cap.

In some embodiments, the wedge locking body 220 may include two distinct sections: a first posterior section 220 and a second anterior section 230. FIG. 9 provides an enlarged view of the second anterior section 230 of the wedge element. The second anterior section 230 may include a flange 232, a groove 234, and a lock 236. The flange 232 is designed to engage the linear track created by the ridges 62 of the hinge mechanism 60 on the intervertebral device 100 upon rotation of the brace 200 into the lock position (as shown in FIG. 7A to 7E). In this manner, the flange 232 resists further rotation of the brace 200. The ridges 62 fit inside the groove 234 and the lock 236 prevents/resists the backward movement of the brace 200.

A posterior cap or wall may be associated with the cruciform bracing or may be independently associated with the expanded intervertebral device, to further stabilize the walls and to obstruct material from displacing from the interior of the device via the posterior portal. In some embodiments, the posterior cap or wall is locked to the perimeter walls with mating interior and/or exterior geometries, with or without a screw lock and detent mechanism.

Additionally, a cable element may be used that extends from one opposing wall to another anteriorly, to mitigate deployment significantly beyond the most stable position of relatively coplanar configuration of the lateral walls in the fully extended position as well as to partially contain material delivered into the intervertebral device from the posterior portal.

Figure 10A:
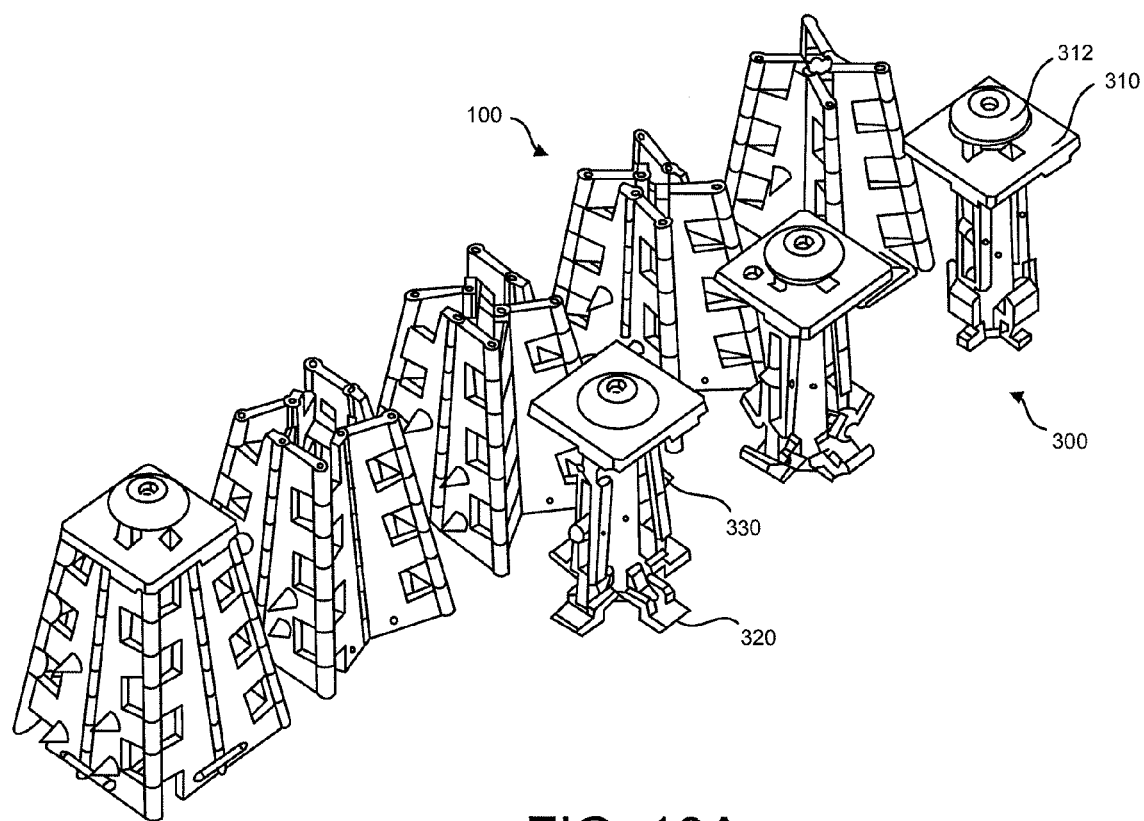
FIG. 10A provides a perspective view of the expansion of an intervertebral device and support brace of the present embodiments.
Figure 10B:
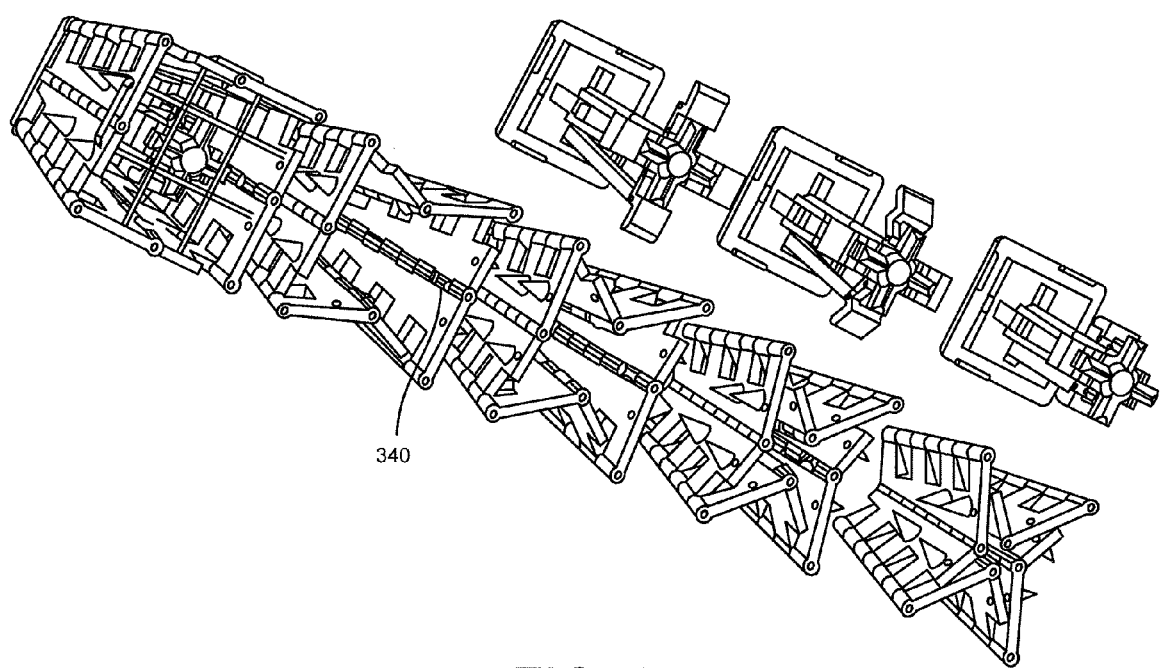
FIG. 10B provides an anterior view of the expansion of an intervertebral device and support brace of the present embodiments.

FIGS. 10A and 10B show a brace 300 according to some embodiments as the brace 300 moves from the collapsed to the fully engaged support position. The brace 300 can include a cap 310 and central screw 310. The cap 310 can be configured to correspond to the posterior end of the implant 100. The brace 300 can be inserted into the interior cavity of the intervertebral device 400. The brace 300 can be in position once the posterior cap 310 engages and aligns to posterior end of the intervertebral device 400. Pressure can be applied to the central screw 312, and the central screw 312 toward the cap 310. The central screw 312 may be locked/snapped into place upon engagement of the cap 310. The pressure applied to the central screw 312 also can cause deployment of the support pads 320, which is connected to the central screw 312 via a lever mechanism 330. The pads 320 can engage walls of the implant and provide support in all four quadrants. The support pads 320 may optionally be configured to engage a lock mechanism 340 on the implant 100 to further prevent the brace from migrating after deployment.

As mentioned above, the peripheral walls can be at least partially expanded prior to insertion of the brace by prying open or expanding the walls from the initial introductory configuration of reduced height and volume to an expanded positioned of increased height and volume. An elongate tool, such as an obturator, can be used. For example, the obturator can include a tapered projecting tip that can have external surface thread form to couple to a complementary threaded entry port at a posterior end of the device. Alternatively or in addition to the obturator, the peripheral walls of the intervertebral device 100 can be at least partially expanded in situ prior to insertion of the brace 200 using an expanding element 1205 positioned on an obturator 1210 (see FIGS. 12A-12B). The walls can be expanded symmetrically in a simultaneous manner, alternatively, the walls can be expanded asymmetrically or in a sequential manner. The obturator 1210 having a tapered distal end 1215 can be inserted such that it inserts through the posterior end of the intervertebral device 100. The distal end 1215 of the obturator 1210 can have a coupling mechanism such as threads such that couple with a complementary threaded entry port near the posterior end of the device 100, such that the obturator 1210 can be used to pull itself into the interior volume of the intervertebral device 100 while urging the expandable element 1205 surrounding an outer surface of the distal end 1215 of the obturator 1210 into the interior volume. The obturator 1210 need not include threads and can be tapped into the entry using another tool. The expandable element 1205 on the distal end 1215 of the obturator 1210 can be inserted through the interior volume towards an anterior region of the interior volume where is can be expanded radially outward. The expandable element 1205 can be formed of an elastomeric material, such as a balloon, that can be pressurized such as with a gas or fluid to hydraulically expand the expandable element 1205. Hydraulic expansion of the expandable element 1205 positioned in the interior volume can urge the peripheral walls of the device towards the second, expanded configuration. An anterior region of the expandable element 1205 can have a larger radially expansion than a more proximal region of the expandable element 1205 to accommodate the wedge-shaped intervertebral device 100. The expandable element 1205 can be positioned on the obturator 1210 near a tapered, projecting tip of the distal end 1215.

Once the intervertebral device 100 is at least partially expanded using the expandable element 1205 on the obturator 1210, the brace 200 can be inserted over the obturator 1210 by virtue of the bore 245 extending through the brace 200 along its longitudinal axis. The brace 200 can be inserted such that an anterior opening 247 to the bore 245 is at least in contact with a proximal region of the expandable element 1205. The expandable element 1205 can be collapsed back down around an outer surface of the obturator 1210 and withdrawn through the bore 245 of the brace 200. The brace 200 can be urged in a more anterior direction to maintain the expanded configuration of the intervertebral device 100 and then locked into position.

The devices described herein can include caudal and cephalad plates that are positioned adjacent to vertebral endplates within an intervertebral disc space. The devices can include at least two lateral walls attached to the caudal and cephalad plates via an articulating mechanism. Any of the plates and walls can be relatively radiolucent. Further, any of the plates and walls can include an external surface that is textured. At least one of the lateral walls can include a hinge element that is restricted from achieving an on-center or over-center articulation position. The devices can be configured to be inserted into an intervertebral disc space in a reduced dimension configuration and subsequently expanded to an enlarged dimension configuration. In the enlarged dimension configuration, materials can be positioned and contained within the internal volume of the device. Such materials can include one or more osteoinductive, osteoproliferative, osteoconductive materials. The materials can extend from an inferior (caudal) vertebral endplate to a superior (cephalad) vertebral endplate. The enlarged dimension configuration can be dimensionally expanded along an axis or arc other than the expansion associated with caudal-cephalad expansion. The devices can further include an internal brace positioned between the plates and the at least two lateral walls. The brace can be compressed by the caudal-cephalad compressive loading of the device along axes extending between the caudal and cephalad plates as well as between at least two lateral walls.

The intervertebral device can be implanted through a relatively small posterior access annulotomy, while providing for lordotic support inducing disc space distraction and an expanded "foot-print" for endplate support.

In some embodiments, the intervertebral device is delivered by an insertion tool that provides relatively smooth boundary surfaces, such that insertion adjacent to nerve roots or durra would be less hazardous. The intervertebral device may further include extensive fenestration of its surfaces, to provide for fibrous, vascular, and osseous in-growth. This will further stabilize the device and facilitate bone growth from endplate to adjacent endplate.

As mentioned above, the intervertebral device can be initially delivered into the disc space, in a collapsed or folded form and then expanded in situ. The intervertebral device may be expanded in situ using a variety of methods, including, but not limited to, hydraulic expansion (e.g., using an expanding balloon), mechanical distraction (e.g., using a wedging tool to pry the walls apart), or an articulating tool (e.g., one that pushes or pulls opposing walls apart).

In some embodiments, the intervertebral device is delivered by an insertion tool or outer sheath that provides relatively smooth boundary surfaces, such that insertion adjacent to nerve roots or durra would be less hazardous. The brace and/or obturator may also be delivered via a sheath.

In some embodiments, the intervertebral device includes extensive fenestration of its surfaces, to provide for fibrous, vascular, and osseous in-growth from neighboring and adjacent vertebrae and/or vertebral endplates. This will further stabilize the device and facilitate bone growth from endplate to adjacent endplate.

According to some embodiments, methods are provided in which an intervertebral device as described herein is introduced into the intervertebral disc space with the hinged walls articulated as to reduce or minimize the cross-sectional delivery area requirement or insertion volume of introduction, with subsequent deployment of the device in an expanded geometry, such that the hinged elements are relatively parallel in their stabilized and/or deployed configuration. The deployment into the expanded geometry can be performed by a separate tool inserted within the interior volume of the device such that the walls of the device are pried open and expanded outward. The walls can be articulated using a wedge-like tool or hydraulic expansion.

Some embodiments provide an interbody intervertebral device indicated for vertebral body replacement or interbody fusion. The intervertebral device may be inserted through an open, or minimally invasive, posterior, anterior, or transforaminal approach into the implantation space to maintain or restore the height of a disc space after a discectomy or other procedure. Fusion of the vertebral bodies may take place over the course of 6-12 months during which it may be desired to maintain an appropriate space between the vertebral bodies.

Some embodiments provide an artificial interbody spinal fusion intervertebral device for insertion within an implantation space formed across the height of a disc space between vertebral bodies of a human spine.

Other embodiments can include a surgical kit for surgery on human spines having vertebral bodies and disc spaces having heights between some of the vertebral bodies, the vertebral bodies having an anterior aspect and a posterior aspect and a depth therebetween. According to one embodiment, a surgical kit can comprise a set of different sized articulating interbody cages for insertion within implantation spaces formed across the heights of the disc spaces.

Another embodiment can include a method of manufacturing an articulating interbody cage for insertion within an implantation space formed across the height of a disc space between vertebral bodies of a human spine, the vertebral bodies having an anterior aspect and a posterior aspect and a depth therebetween.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. A device comprising:
   caudal and cephalad plates that are configured to be positioned adjacent to vertebral endplates within an intervertebral disc space;
   at least two lateral walls attached to the caudal and cephalad plates via an articulating mechanism, wherein at least one of the lateral walls includes a hinge element,
   wherein the device is configured to be inserted into the intervertebral disc space in a reduced dimension configuration and subsequently expanded to an enlarged dimension configuration, and
   wherein the hinge element is restricted to an under-center rotation position when the device is fully expanded to the enlarged dimension configuration.

2. The device of claim 1, wherein one or more of the caudal plate, cephalad plate, and lateral walls is relatively radiolucent.

3. The device of claim 1, further comprising one or more osteoinductive, osteoproliferative, osteoconductive materials positioned internal to the device and extending from a caudal vertebral endplate to a cephalad vertebral endplate.

4. The device of claim 1, wherein one or both of the caudal and cephalad plates comprises an external textured surface.

5. The device of claim 1, further comprising an insertable internal brace configured to stabilize the under-center rotation position.

6. The device of claim 1, wherein the at least one of the lateral walls comprises:
   a first wall portion having a first block element and a first overhang; and
   a second wall portion having a second block element and a second overhang,
   wherein the first block element is configured to interdigitate with the second block element forming the hinge element.

7. The device of claim 6, wherein upon articulation of the first and second wall portions relative to one another around the hinge element, the first overhang is configured to contact the second wall portion and the second overhang is configured to contact the first wall portion.

8. The device of claim 7, wherein contact between the first and second overhangs with the first and second wall portions restricts articulation around the hinge element to hypo-extension of the device in the enlarged dimension configuration.

9. The device of claim 6, wherein at least one of the first wall portion and the second wall portion further comprises a plurality of ridge elements that form a linear track upon expansion of the intervertebral device to the enlarged dimension configuration.

10. The device of claim 1, further comprising a removable brace element configured to be positioned within an interior volume of the device between the plates and the at least two lateral walls such that caudal-cephalad compressive loading of the device results in compression of the internal brace along axes extending between the caudal and cephalad plates as well as between the at least two lateral walls.

11. The device of claim 10, wherein the brace element has a fixed dimension.

12. The device of claim 10, wherein the brace element prevents the device from articulating around the hinge element towards the reduced dimension configuration.

13. The device of claim 10, wherein the brace element comprises fenestrations configured to permit growth of tissue from one vertebral endplate to a second vertebral endplate.

14. The device of claim 1, wherein the enlarged dimension comprises expansion of the device in a first dimension.

15. The device of claim 14, wherein the enlarged dimension comprises expansion of the device in a second dimension.

16. The device of claim 15, wherein the first dimension comprises a caudal-cephalad dimension and the second dimension comprises a medial-lateral dimension.

17. The device of claim 1, wherein the device creates a desired lordosis in the spine.

18. The device of claim 1, wherein the at least two lateral walls are trapezoidal in shape.

19. The device of claim 1, wherein an outer surface of the cephalad plate and an outer surface of the caudal plate comprise projection elements that engage the respective superior and inferior vertebral endplates.

* * * * *